United States Patent
Johansson

(10) Patent No.: US 11,779,383 B2
(45) Date of Patent: Oct. 10, 2023

(54) STABILIZING PRESSURE IN CRYOGENIC DEVICES

(71) Applicant: Pacira CryoTech, Inc., Parsippany, NJ (US)

(72) Inventor: Eric Theodore Johansson, Dublin, CA (US)

(73) Assignee: Pacira CryoTech, Inc., Tampa, FL (US)

( * ) Notice: Subject to any disclaimer, the term of this patent is extended or adjusted under 35 U.S.C. 154(b) by 372 days.

(21) Appl. No.: 17/102,757

(22) Filed: Nov. 24, 2020

(65) Prior Publication Data

US 2021/0161577 A1 Jun. 3, 2021

Related U.S. Application Data

(60) Provisional application No. 62/943,017, filed on Dec. 3, 2019.

(51) Int. Cl.
*A61B 18/02* (2006.01)
*A61B 18/00* (2006.01)

(52) U.S. Cl.
CPC .... *A61B 18/02* (2013.01); *A61B 2018/00041* (2013.01); *A61B 2018/0047* (2013.01); *A61B 2018/00744* (2013.01); *A61B 2018/0262* (2013.01); *A61B 2018/0293* (2013.01)

(58) Field of Classification Search
CPC .......... A61B 18/02; A61B 2018/00262; A61B 2018/0293
See application file for complete search history.

(56) References Cited

U.S. PATENT DOCUMENTS

| | | |
|---|---|---|
| 7,713,266 B2 | 5/2010 | Elkins et al. |
| 7,850,683 B2 | 12/2010 | Elkins et al. |
| 7,998,137 B2 | 8/2011 | Elkins et al. |
| 8,298,216 B2 | 10/2012 | Burger et al. |
| 8,409,185 B2 | 4/2013 | Burger et al. |
| 8,461,108 B2 | 6/2013 | Hsu et al. |
| 9,039,688 B2 | 5/2015 | Palmer, III et al. |
| 9,066,712 B2 | 6/2015 | Reynolds et al. |
| 9,072,498 B2 | 7/2015 | Elkins et al. |
| 9,241,753 B2 | 1/2016 | Fourkas et al. |
| 9,254,162 B2 | 2/2016 | Burger et al. |
| 9,295,512 B2 | 3/2016 | Allison et al. |

(Continued)

FOREIGN PATENT DOCUMENTS

WO 2007076123 7/2007

*Primary Examiner* — Daniel W Fowler
(74) *Attorney, Agent, or Firm* — Kilpatrick Townsend & Stockton LLP

(57) ABSTRACT

Methods for stabilizing pressure within a cryogenic device include receiving a flow rate value corresponding to an expected average mass flow rate of a cryogen through a needle probe of the cryogenic device during a cryotherapy treatment cycle; determining, based on the flow rate value, a target heater power to be applied to a heater associated with the cryogenic device for a treatment cycle, wherein the heater is configured to heat the cryogen; receiving an input for the treatment cycle; causing the cryogen to flow for a period of time toward the needle probe in response to the input; and apply the target heater power to the heater during the treatment cycle so as to heat the cryogen and stabilize pressure within the cryogenic device.

20 Claims, 13 Drawing Sheets

(56) References Cited

U.S. PATENT DOCUMENTS

| | | |
|---|---|---|
| 9,314,290 B2 | 4/2016 | Fourkas et al. |
| 9,345,526 B2 | 5/2016 | Elkins et al. |
| 9,610,112 B2 | 4/2017 | Karnik et al. |
| 9,668,800 B2 | 6/2017 | Karnik et al. |
| 10,016,229 B2 | 7/2018 | Carnell et al. |
| 10,085,789 B2 | 10/2018 | Carnell et al. |
| 10,085,881 B2 | 10/2018 | Karnik et al. |
| 10,130,409 B2 | 11/2018 | Hinton et al. |
| 10,314,739 B2 | 6/2019 | Allison et al. |
| 10,470,813 B2 | 11/2019 | Allison et al. |
| 10,596,030 B2 | 3/2020 | Karnik et al. |
| 10,888,366 B2 | 1/2021 | Allison |
| 2002/0045894 A1* | 4/2002 | Joye ............... A61B 18/02 606/21 |
| 2011/0162390 A1 | 7/2011 | Littrup et al. |
| 2012/0089211 A1 | 4/2012 | Curtis et al. |
| 2012/0259322 A1 | 10/2012 | Fourkas et al. |
| 2015/0018810 A1 | 1/2015 | Baust et al. |
| 2015/0148791 A1* | 5/2015 | Birdsall ............ A61B 18/02 606/22 |
| 2016/0038212 A1 | 2/2016 | Ryba et al. |
| 2016/0183998 A1 | 6/2016 | Fourkas et al. |
| 2017/0354461 A1* | 12/2017 | Rothman ............ G01R 5/26 |
| 2018/0116705 A1 | 5/2018 | Lee et al. |
| 2018/0303535 A1* | 10/2018 | Yu ............... A61B 18/02 |
| 2019/0038459 A1 | 2/2019 | Karnik et al. |
| 2019/0142494 A1 | 5/2019 | Cross et al. |

\* cited by examiner

STABILIZING PRESSURE IN CRYOGENIC DEVICES

CROSS REFERENCE TO RELATED APPLICATION DATA

The present application claims the benefit of U.S. Provisional Appln No. 62/943,017 filed Dec. 3, 2019; the full disclosure which is incorporated herein by reference in its entirety for all purposes.

RELATED FIELDS

Devices, systems, and methods for cooling tissue for therapeutic purposes, including nerves for treating pain.

BACKGROUND

The present disclosure is generally directed to medical devices, systems, and methods for cryotherapy. More specifically, the present disclosure relates to cryogenically cooling target tissues of a patient so as to degenerate, inhibit, remodel, or otherwise affect a target tissue to achieve a desired change in its behavior or composition. Cryogenic cooling of neural tissues has been shown to be effective in treating a variety of indications including pain (e.g., occipital and other neuralgias, neuromas, osteoarthritis pain), spasticity, and joint stiffness, among others. For example, cooling neural tissues has been found to degenerate or inhibit nerves that are instrumental in causing these conditions. Cryogenic cooling has also been employed to address cosmetic conditions, for example, by inhibiting undesirable and/or unsightly effects on the skin (such as lines, wrinkles, or cellulite dimples) or on other surrounding tissue.

In light of the above, cryogenic devices with needle probes have emerged as a mode of therapeutically cooling target tissues for treating a variety of indications. The needle probes of such devices are typically inserted into a patient's skin adjacent to a target tissue. Some cryogenic devices may include a cryogen that may be either injected into the target tissue via openings in needles of their needle probes, such that the target tissue is cooled directly by the cryogen. Other cryogenic probes may include closed needle tips, in which case the needles may be cooled (e.g., by a flow of the cryogen), and the target tissue adjacent to the cooled needles may thereby be cooled by conduction. Cryogenic probes have proved to be effective in creating cryozones within a patient at or around target tissues with precision, convenience, and reliability. A cryozone may be a volume of tissue that is cooled by one or more needles of a cryogenic probe (e.g., a volume of tissue near or around a distal portion of the needles). For example, a cryozone may be a volume of tissue that is cooled so as to freeze the tissue within the volume (e.g., the cryozone may be defined by an approximately 0° C. (or other suitable temperature) isotherm that may form around a needle of the cryogenic probe).

BRIEF SUMMARY

This disclosure relates to improved medical devices, systems, and methods. Many of the devices and systems described herein will be beneficial for cryotherapy using a cryogenic device.

In some embodiments, a method may include receiving a first flow rate value, wherein the first flow rate value corresponds to an expected average mass flow rate of a cryogen through a first needle probe of the cryogenic device during a cryotherapy treatment cycle. The method may further include determining, based on the first flow rate value, a first target heater power to be applied to a heater associated with the cryogenic device for a first treatment cycle. The method may further include receiving an input for the first treatment cycle. The method may include causing the cryogen to flow for a period of time toward the first needle probe in response to the input and applying the first target heater power during the first treatment cycle so as to heat the cryogen and stabilize pressure within the cryogenic device during or after the first treatment cycle (or before the first treatment cycle in some embodiments). Such a method may be used, for example, to stabilize pressure within the cryogenic device during a cryotherapy treatment.

In some embodiments, the first target heater power is defined such that an average rate of change in pressure during a cooling phase of the first treatment cycle remains within a predetermined range. In some embodiments, the first flow rate value is received by a processor of the cryogenic device from the first needle probe.

In some embodiments, the heater is coupled to a cryogen cartridge associated with the cryogenic device. In some embodiments, the cryogenic device includes a handpiece portion, and the cryogen cartridge and the first needle probe may be directly coupled to the handpiece portion.

In some embodiments, the method may include determining a target duty cycle (or a pulse width modulation percentage (PWM %)) necessary for applying the first target heater power. In these embodiments, applying the first target heater power may include engaging the heater for the target duty cycle. In some embodiments, the target duty cycle is determined based on an output of an equation: Duty Cycle=$P_{Target} \times (R_{Heater}/V_{Heater}^2)$, wherein $P_{Target}$ is the first target heater power, $R_{Heater}$ is a resistance of the heater, and $V_{Heater}$ is a voltage across the heater. In some embodiments, the method includes monitoring a voltage of a power source coupled to the heater so as to estimate a real-time value for $V_{Heater}$.

In some embodiments, applying the first target heater power comprises adjusting an amount of current or voltage applied to the heater.

In some embodiments, the method includes receiving pressure data from a pressure sensor of the cryogenic device during the first treatment cycle; calculating, based on the received pressure data, an average rate of change in pressure during a cooling phase of the first treatment cycle; and calculating a second target heater power for a second treatment cycle, wherein the second target heater power is calculated at least in part by adjusting the first target heater power upward or downward by an adjustment value based on the average rate of change in pressure. In some embodiments, the method may include determining that the average rate of change in pressure is negative and beyond a predetermined range, wherein the second target heater power is calculated at least in part by adjusting the first target heater power upward by the adjustment value. In some embodiments, the method may include determining that the average rate of change in pressure is positive and beyond a predetermined range, wherein the second target heater power is calculated at least in part by adjusting the first target heater power downward by the adjustment value. In some embodiments, the adjustment value is determined based on a magnitude of the average rate of change in pressure.

In some embodiments, the method may include determining that the average rate of change in pressure has a magnitude greater than a threshold magnitude. The method may further include generating, based on the determination, a notification indicating an issue with the cryogenic device. In some embodiments, the average rate of change in pressure may be determined to be negative, and the notification may identify the issue as a depleted cryogen source based on the average rate of change in pressure. In some embodiments, the average rate of change in pressure may be determined to be positive, and the notification may identify the issue as a blocked or impeded cryogen pathway based on the average rate of change in pressure.

In some embodiments, the method may include determining a first pressure of the cryogenic device prior to a cooling cycle of the first treatment cycle; determining a second pressure of the cryogenic device prior to a cooling cycle of a second treatment cycle; calculating a second target heater power for the second treatment cycle. In some embodiments, the second target heater power is calculated at least in part by: adjusting the first target heater power upward when the second pressure is lower than the first pressure; or adjusting the first target heater power downward when the second pressure is greater than the first pressure.

In some embodiments, the method may include replacing the first needle probe with a second needle probe; receiving a second flow rate value, wherein the second flow rate value corresponds to an expected average mass flow rate of a cryogen through the second needle probe during a cryotherapy treatment cycle; and determining, based on the second flow rate value, a new target heater power to be applied by the heater for a treatment cycle to be performed with the second needle probe.

In some embodiments, the first treatment cycle includes a cooling phase and a recovery phase. In some embodiments, the first target heater power is applied during the cooling phase.

A cryogenic device is described for effecting the methods described herein. In some embodiments, the cryogenic device may include a cryogen source including a pressurized cryogen; a cryogen pathway configured to direct the cryogen toward a needle probe comprising one or more needles, wherein the cryogen is configured to deliver cryotherapy to a target tissue via the one or more needles; a heater; and a processor. In some embodiments, the processor may be configured to receive a first flow rate value, wherein the first flow rate value corresponds to an expected average mass flow rate of a cryogen through a first needle probe of the cryogenic device during a cryotherapy treatment cycle; determine, based on the first flow rate value, a first target heater power to be applied to a heater associated with the cryogenic device for a first treatment cycle, wherein the heater is configured to heat the cryogen; receive an input for the first treatment cycle; cause the cryogen to flow for a period of time toward the first needle probe in response to the input; and apply the first target heater power to the heater during the first treatment cycle so as to heat the cryogen and stabilize pressure within the cryogenic device during or after the first treatment cycle.

DETAILED DESCRIPTION

The present disclosure describes features of cryogenic devices that may be used to deliver a cryotherapy to patients. In some embodiments, the described cryogenic devices may include needles for delivering cryotherapy subcutaneously to target particular tissues for treating a variety of conditions. For example, the cryogenic devices may include needles that are configured to be inserted near peripheral nerves to deliver cryotherapy to the peripheral nerves to treat pain, spasticity, or other such conditions that may be improved by such therapy. More information about the use of cryotherapy for alleviation of pain or spasticity may be found in U.S. Pat. No. 8,298,216 filed Nov. 14, 2008; U.S. Pat. No. 9,610,112 filed Mar. 18, 2014; U.S. Pat. No. 10,085,789 filed Mar. 13, 2017; and U.S. Patent Publn No. 20190038459 filed Sep. 14, 2018, the full disclosures of which are incorporated herein by reference in their entirety for all purposes. The cryogenic devices may also be used for prophylactic treatment such as disruption or prevention of neuromas, for example, as described in U.S. Pat. No. 10,470,813 filed Mar. 14, 2016, the full disclosure of which is incorporated herein by reference in their entirety for all purposes.

Figure 1A:
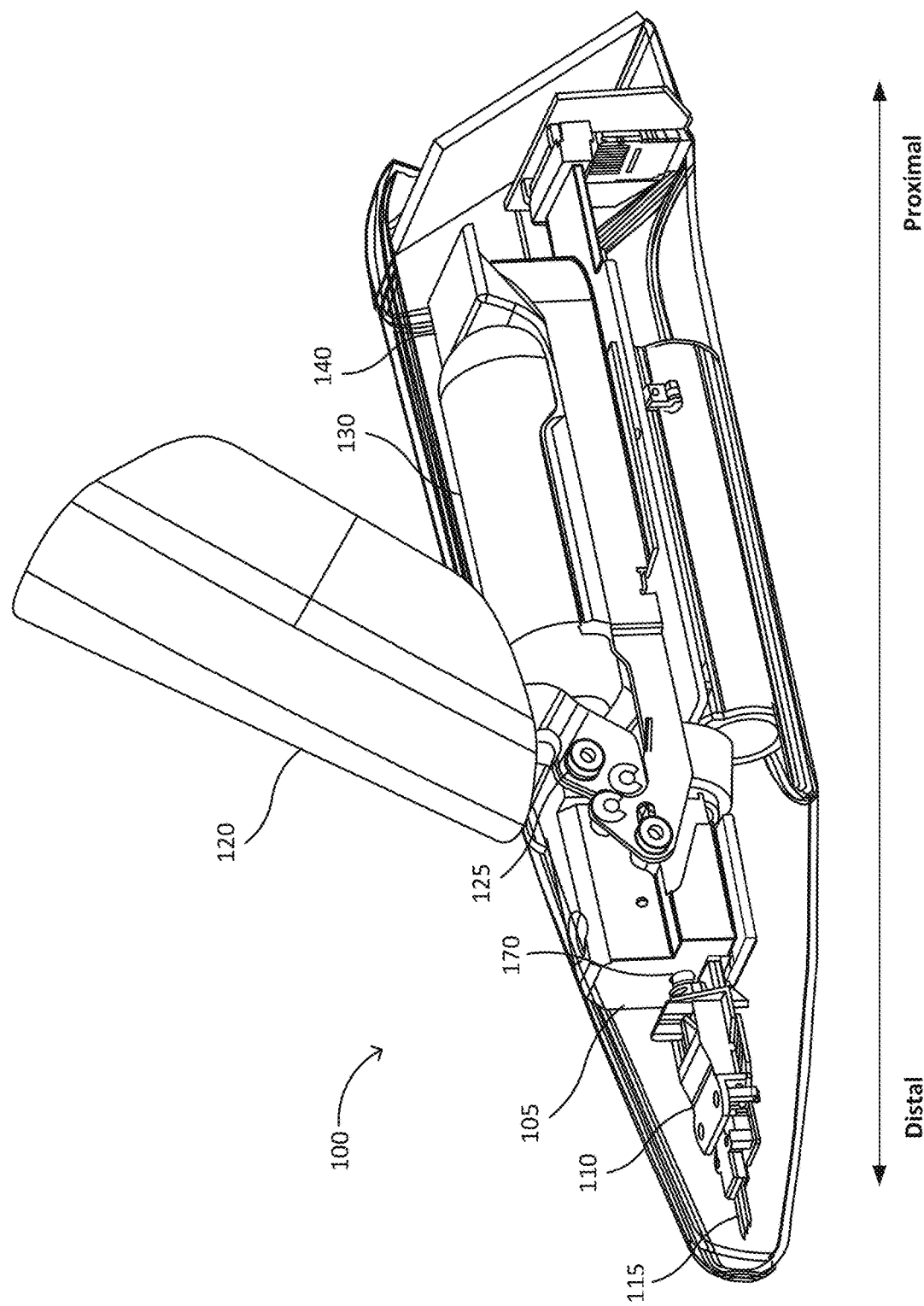
FIGS. 1A-1B illustrate an example embodiment of a cryogenic device including a cartridge holder for holding a cryogen cartridge and a needle probe.
Figure 1B:
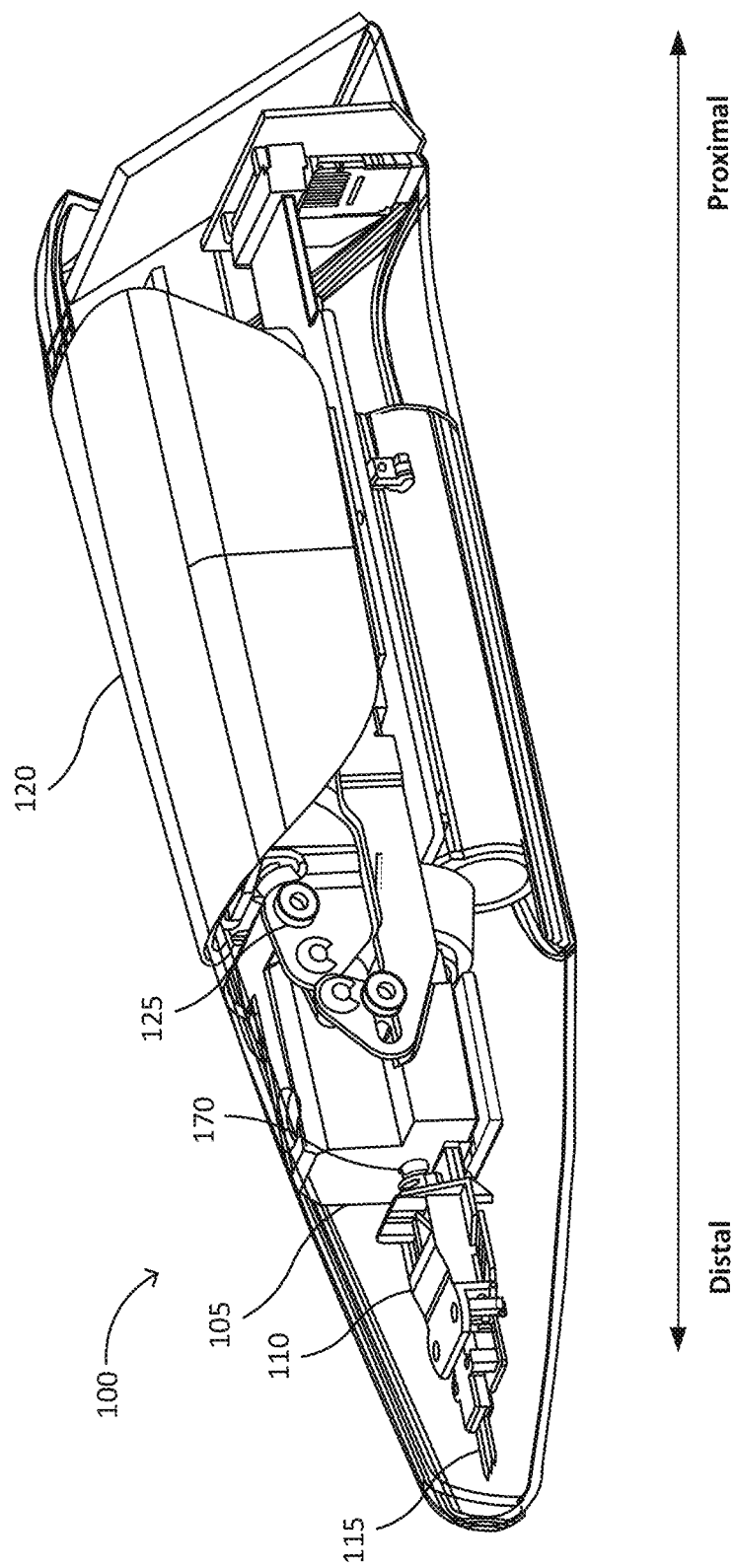

FIGS. 1A-1B illustrate an example embodiment of a cryogenic device 100 including a cartridge holder 140 for holding a cryogen cartridge 130 and a needle probe 110. As shown in the illustrated example embodiment, the cryogenic device 100 may be a self-contained handpiece suitable for being grasped and manipulated by an operator's hand. In other embodiments, the cryogenic device may include physically separated components. For example, the cryogenic device may include a handpiece including a needle probe and a cryogen cartridge that is separated from the handpiece. In some embodiments, the cryogenic device 100 may have a multi-part (e.g., a two-part) housing, with the needle probe 110 disposed within a separate probe housing that may be coupled to a housing of a handpiece portion. In other embodiments, the needle probe 110 may not be disposed within a separate housing and may be configured to be inserted directly into the housing of the cryogenic device 100. As an example, the cryogenic device 100 in at least some of these embodiments may have a single housing.

In some embodiments, the cryogen cartridge 130 may be a disposable cartridge filled with a cryogen (e.g., nitrous oxide, fluorocarbon refrigerants, and/or carbon dioxide). The cryogen cartridge 130 may be pressurized, such that the cryogen within is maintained at a relatively high pressure. In some embodiments, the cryogenic device 100 may include a cartridge door 120 for accessing the cryogen cartridge 130 (e.g., to replace it). The cartridge door 120 may be configured to move from an open position for allowing the cartridge holder 140 to receive a cryogen cartridge 130 to a closed position for securing the cryogen cartridge 130 within the housing of the cryogenic device 100. For example, as illustrated in FIG. 1A-1B, the cartridge door 120 may be configured to swivel around swivel point 125 to allow access to the cryogen cartridge 130. In this example, a user may open the cartridge door 120 (e.g., when the user notices that the cryogen cartridge 130 is empty) as shown in FIG. 1A, remove the cryogen cartridge 130 from the cartridge holder 140, insert a new cryogen cartridge 130 into the cartridge holder 140, and close the cartridge door 120 as shown in FIG. 1B.

In some embodiments, cryotherapy using the cryogenic device 100 may be performed in discrete treatment cycles. For example, a processor of the cryogenic device 100 may be configured to control the cryogen flow (e.g., by operating a supply valve). The processor may be configured to provide a treatment cycle in response to a treatment instruction. The treatment cycle may include a cooling phase (where cryogen is flowed to the needles) and a recovery phase (where cryogen is not flowed to the needles). For example, a treatment cycle may include a cooling phase with a duration of 20-65 seconds, followed by a recovery phase with a duration of 10-60 seconds. As another example, it may be particularly advantageous for a treatment cycle including a cooling phase with a duration of 33-60 seconds, followed by a recovery phase with a duration of 15-45 seconds. During the cooling phase, a cryozone may be formed in a tissue around the needle (e.g., at a distal tip of the needle) when the cryogen flows to the needles. The cryozone may be defined, for example, by a 0° C. isotherm (e.g., cooling zone) such that the cryozone includes a frozen "iceball" of tissue. In some embodiments, the cryogen may be made to vaporize within the needle lumens to cause the creation of a cryozone (e.g., by leveraging the Joule-Thomson effect). During the recovery phase, cryogen flow is ceased such that the needles are caused to warm up to a baseline temperature. More information about treatment cycles may be found in U.S. Patent Publn No. 20190038459 filed Sep. 14, 2018, which is incorporated herein by reference in its entirety for all purposes.

In some embodiments, the cryogenic device 100 may include a skin warmer, which may be a heating element for warming the skin to, for example, reduce collateral damage to the skin. The skin warmer may be activated prior to or during a treatment cycle for a prescribed heating duration. For example, the skin warmer may be activated for a pre-heating period of a particular duration prior to a treatment cycle. More information about cryogenic devices with skin warmers may be found in U.S. Pat. No. 10,470,813 filed Mar. 14, 2016, which is incorporated herein by reference in its entirety for all purposes.

Figure 2A:
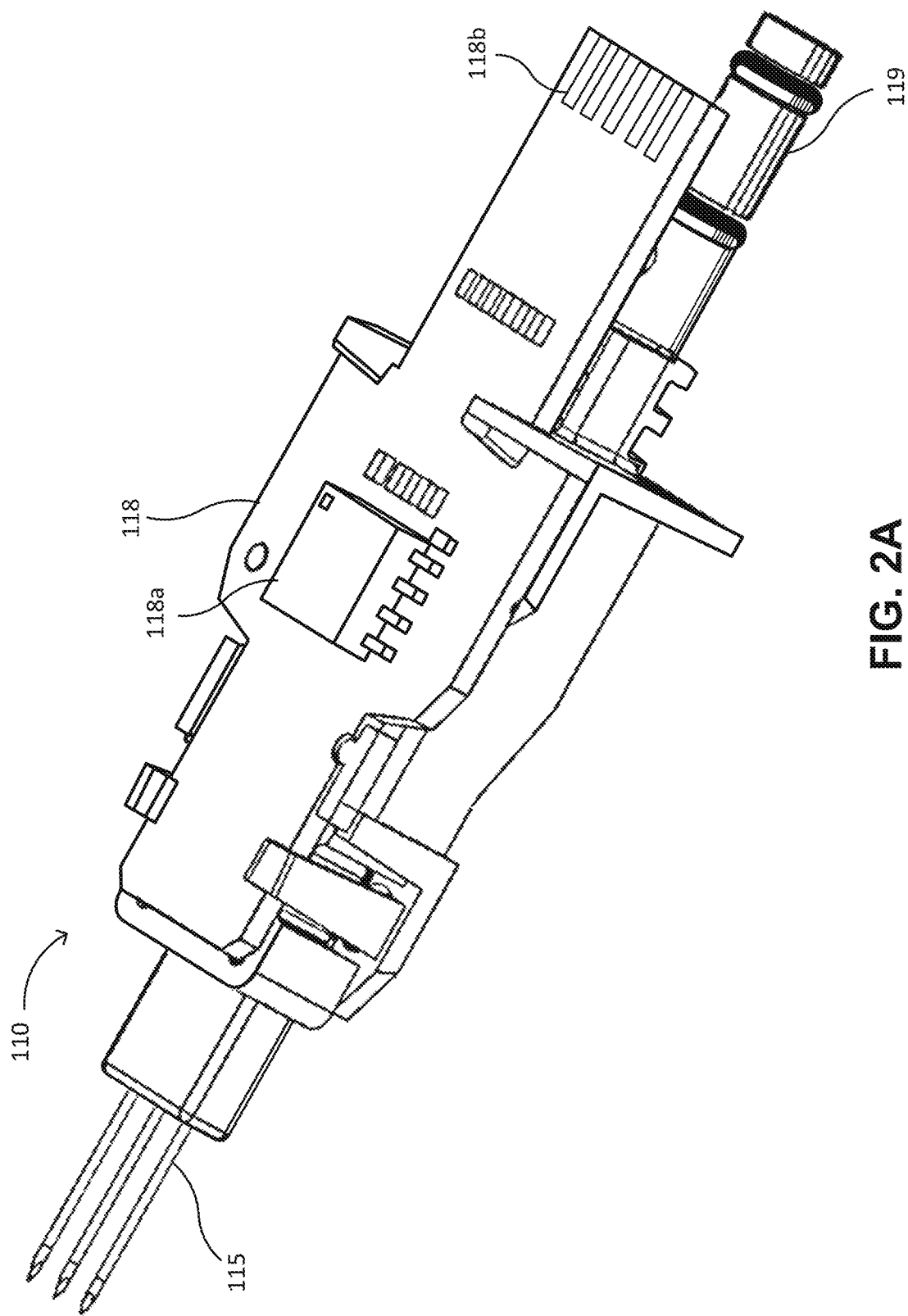
FIG. 2A illustrates an example needle probe.

FIG. 2A illustrates an example needle probe 110. In some embodiments, the illustrated needle probe 110 may have an external housing (not illustrated). In some embodiments, the needle probe 110 may include one or more needles 115 suited for penetration into a patient's skin adjacent to a target tissue (e.g., nerve tissue). For example, as illustrated in FIG. 2A, the needle probe 110 may include three needles 115. Each of the needles of the needle probe 110 may have needle lumens disposed therein (not illustrated). In some embodiments, the needles 115 may have closed tips without any distal openings, such that they do not allow for the ejection of cryogen from the distal end of the needles 115. In these embodiments, the needles 115 themselves are cooled and adjacent target tissue is thereby cooled by conduction. For example, the needles may have needle lumens into which cryogen may be flowed, thereby cooling the needles. In other embodiments, the needles 115 may have open tips, in which case a target tissue may be cooled by injecting a cryogen into a patient within or adjacent to the target tissue. In some embodiments, the needle probe 110 may include a probe extension 119 that is configured to be securable to the probe receptacle 170. When the needle probe is secured to the probe receptacle 170, the probe extension 119 extends proximally toward the proximal end of the cryogenic device (for illustrative purposes, proximal and distal directions are indicated in FIG. 1A). Referencing FIG. 2A, the probe extension 119 may have a probe lumen (not illustrated) disposed therein, the probe lumen extending from a proximal end to a distal end. When the needle probe is secured to the probe receptacle, the probe lumen may be fluidically coupled to a cryogen pathway that extends from the cryogen cartridge 130 toward the probe receptacle 170 for delivering cryogen to the needles. The probe lumen may be coupled to needle lumens of the needles 115 at the distal end of the cryogenic device, such that a cryogen may be allowed to pass through the probe lumen and into the needle lumens (e.g., to cool the needle tips). In some embodiments, cryogen may be vented (e.g., proximally) after cooling the needles. In some embodiments, cryogen may be repeatedly and sequentially flowed into needle lumens and vented from the needle lumens (e.g., during one or more treatment cycles).

In some embodiments, the cryogenic device 100 may be a smart device that includes a first processor (e.g., located within the handpiece and apart from the needle probe 110) to assist the operator with performing a treatment. In some embodiments, the needle probe 110 may be a smart probe. In these embodiments, the needle probe 110 may include a printed circuit board assembly (PCBA). As illustrated in FIG. 2A, the PCBA may include a second processor 118a. In some embodiments, the PCBA may also include a memory component. The PCBA may further include one or more connectors 118b (e.g., a card edge connector) that electrically couple the needle probe 110 to the remainder of the cryogenic device 100 (e.g., the handpiece portion). For example, when a needle probe is received by the probe receptacle 170, a portion of the PCBA 118 (including the connectors 118b) may be received by a port in the handpiece portion.

Figure 2B:
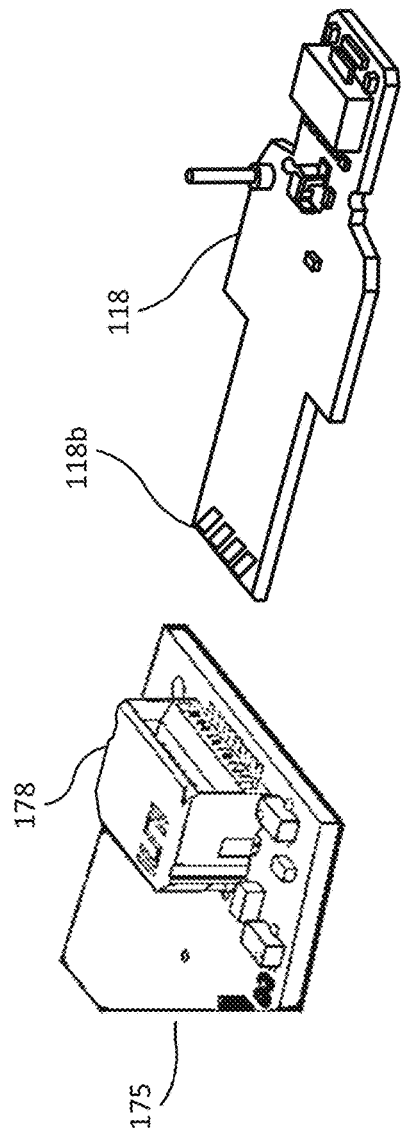
FIGS. 2B-2C illustrate an example embodiment of a port of a PCBA of a handpiece portion receiving a proximal portion of a PCBA of a needle probe.
Figure 2C:
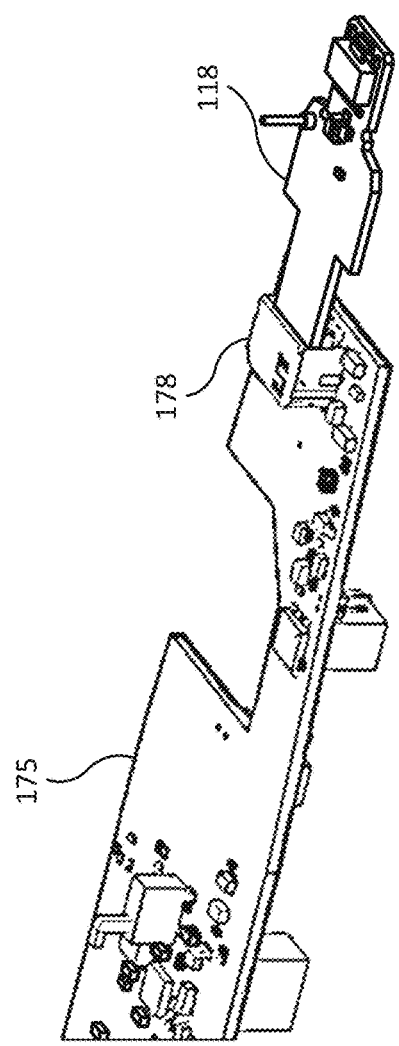

FIGS. 2B-2C illustrate an example embodiment of a port 178 of a PCBA 175 of the handpiece portion receiving the proximal portion of a PCBA 118 of the needle probe 110. As illustrated in the example embodiment of FIGS. 2B-2C, the connectors 118b of the PCBA 118 may be configured to slide into an opening of the port 178 of the PCBA 175 of the handpiece portion.

Once the PCBA 118 of the needle probe 110 is connected to the PCBA 175 of the handpiece portion, the needle probe 110 may be able to transmit and/or receive information to/from the handpiece portion (e.g., via the second processor 118a). In some embodiments, the needle probe 110 may transmit a probe descriptor (e.g., to the first processor) that may, among other things, identify a corresponding probe type of the needle probe. For example, the probe descriptor may identify the number of needles (e.g., a single-needle probe, a three-needle probe, a five-needle probe), the lengths of needles, the configuration of needles (e.g., a rectangular array, a square array, elliptical, circular, triangular, a three-dimensional shape such as an inverted pyramid shape), an average mass flow rate of cryogen through the needle probe, a pre-heating period duration during which a skin warmer of the cryogenic device 100 is activated, a cooling phase duration during which a cryogen is delivered to the needle probe 110, a recovery phase duration during which a valve is shut off so as to prevent further cryogen delivery to the needle probe 110, or any other suitable characteristics or parameters that may be specified for operation of the needle probe 110. Probe descriptors and particular types of parameters that may be included therein are further discussed below. More information about smart cryogenic devices and smart tips may be found in U.S. Pat. No. 10,130,409 filed Nov. 20, 2018, which is incorporated by reference herein in its entirety for all purposes.

Figure 3A:
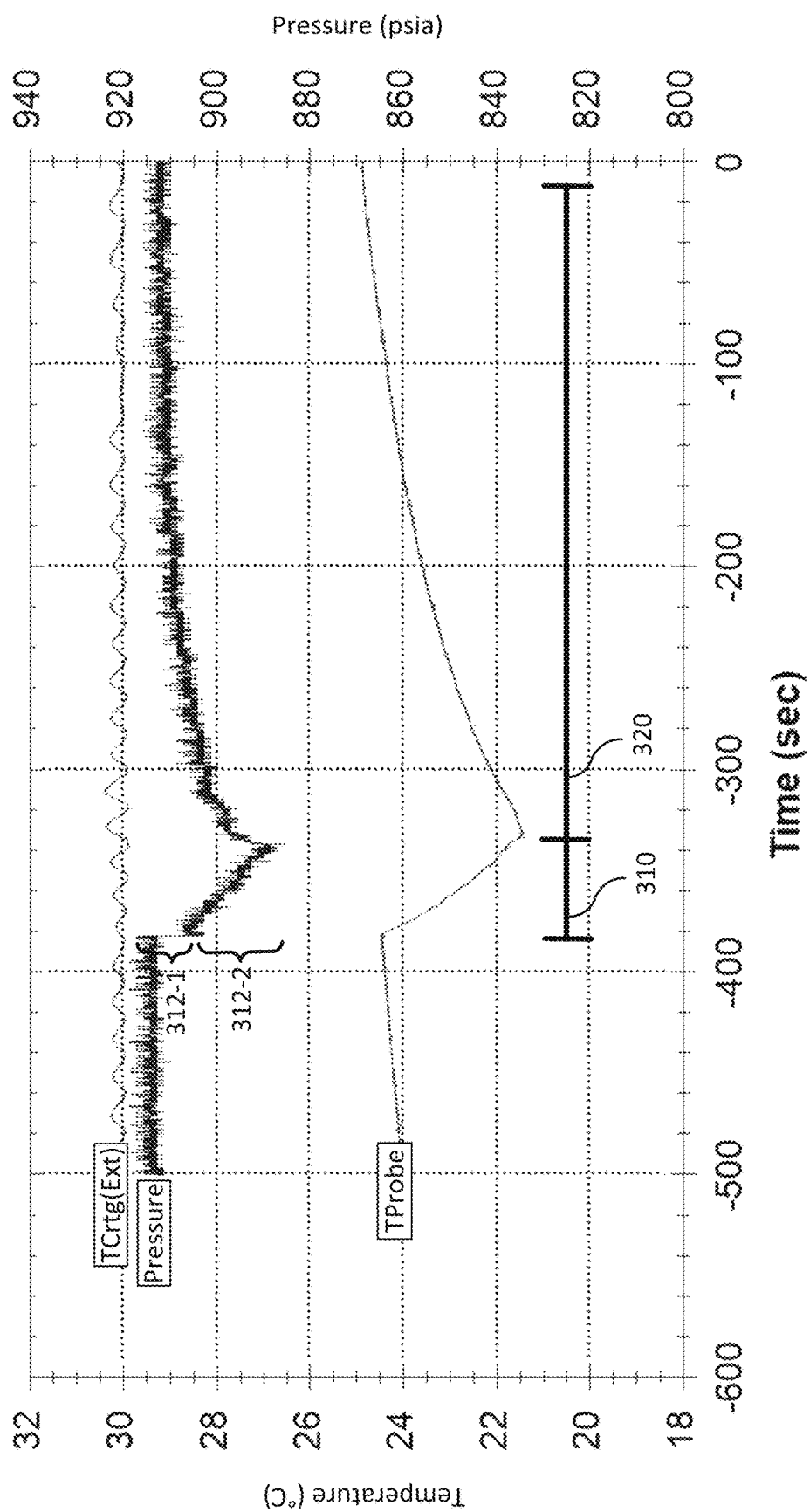
FIG. 3A illustrates an example graph reflecting pressure and temperature associated with the cryogenic device during a single treatment cycle, where a heater heats an exterior of the cryogen cartridge to maintain a relatively constant temperature at the exterior of the cryogen cartridge.

FIG. 3A illustrates example pressure/temperature curves reflecting pressure and temperature associated with the cryogenic device 100 during a single treatment cycle, where a heater heats an exterior of the cryogen cartridge 130 to maintain a relatively constant temperature at the exterior of the cryogen cartridge 130. Referencing FIG. 3A, the treatment cycle may begin with a cooling phase 310, which may be followed by a recovery phase 320. The line labeled TProbe in FIG. 3A indicates temperature at the needle probe 110. The line labeled Pressure indicates pressure of cryogen within the cryogenic device 100. This pressure may be measured, for example, by one or more pressure sensors upstream or downstream of a supply valve through which cryogen is flowed. The line labeled TCrtg(Ext) indicates temperature at the exterior of the cryogen cartridge 130, as may be measured by, for example, one or more temperature sensors positioned near or adjacent to the cryogen cartridge 130. As illustrated, temperature at the needle probe 110 is caused to decrease during the cooling phase 310 as increasing amounts of cryogen is flowed to lumens of the needle probe 110. In FIG. 3A (and subsequent figures illustrating pressure/temperature curves within this disclosure) TProbe and TCrtg(Ext) lines are to be read with reference to the "Temperature (° C.)" axis, and the Pressure line is to be read with reference to the "Pressure (psia)" axis. In some embodiments, cryogen within the cryogen cartridge 130 may be pressurized to be at a baseline pressure value. For example, as illustrated in FIG. 3A, the baseline pressure value may be around 910 pounds per square inch absolute (psia). As cryogen is released during the cooling phase 310 from the pressurized cryogen cartridge 130 and caused to flow along the cryogen pathway, the decrease of cryogen within the cryogen cartridge 130 may cause pressure within the cryogen cartridge 130 to decrease relative to the baseline pressure. Incidentally, this pressure reduction may also accompanied by a temperature reduction. This temperature drop may be due to a cryogen phase change that occurs. The cryogen may be pressurized within the cryogen cartridge 130 such that it is maintained in a mostly liquid phase. As the cryogen is released from the cryogen cartridge 130 and pressure decreases as a result, an amount of the liquid cryogen may undergo a phase change from liquid to gas (e.g., liquid $N_2O$ may boil due to the reduction in pressure and vaporize into gaseous $N_2O$), which is an endothermic phase change that draws heat from the surroundings and ultimately causes the remaining liquid cryogen to be cooled. The reduction in pressure during a treatment cycle is illustrated by the Pressure line in the example of FIG. 3A. As illustrated by bracket 312-1 in FIG. 3A, when the cooling phase 310 of the treatment cycle begins, pressure initially drops by approximately 10 psia as cryogen is released from the cryogen cartridge 130 (e.g., when a supply valve is opened). In the example illustrated in FIG. 3A, the pressure continues to drop during the remainder of the cooling phase, with the pressure dropping approximately 20 psia. This continued drop in pressure is denoted by bracket 312-2. The result is an overall drop in pressure of approximately 30 psia (10 psia+20 psia).

The pressure of cryogen in the cryogen cartridge 130 may be important in that the pressure of the cryogen affects the flow rate of cryogen to the needle probe 110. A significant pressure decrease may result in a decrease in the amount of cryogen that is delivered during a treatment cycle to the needles of a needle probe 110 and/or the amount of cryogen that is vaporized within the needles of the needle probe 110, which ultimately affect the characteristics of the cryozone that forms due to the resultant cooling. A decrease in pressure may result in the formation of a cryozone having a volume that is smaller than optimal for example.

In some embodiments, the cryogenic device 100 may actively increase the temperature of cryogen within the cryogen cartridge 130 so as to increase pressure of the cryogen, and thereby compensate for any decreases in pressure. In some embodiments, the cryogenic device 100 may include a heater for actively increasing the temperature of the cryogen. By increasing cryogen temperature, cryogen pressure is caused to increase, with the exact amounts of pressure increase being based on intrinsic properties of the cryogen as may be characterized in its respective liquid-gas phase transition curve (e.g., for $N_2O$, by the liquid-gas phase transition curve of $N_2O$, which is well-known). For example, as discussed below, one or more heaters may be placed along an exterior of the cryogen cartridge 130 to apply heat to the cryogen cartridge 130. FIG. 3A illustrates one approach of increasing pressure by applying a relatively low amount of heat to the cryogen cartridge 130 to maintain the exterior of the cryogen cartridge 130 at a relatively constant temperature over an entire period of use of the cryogenic device 100 (e.g., over the course of multiple treatment cycles). In this illustrated example, the TCrtg(Ext) line indicates that temperature at the exterior of the cryogen cartridge 130 is maintained at approximately 30° C. by, for example, turning a heater ON or OFF at a relatively constant duty cycle, irrespective of whether a cooling phase or a recovery phase is occurring. A duty cycle (or pulse width modulation percent (PWM %)) may be expressed as a fraction or a percentage of one period during which the heater is turned ON (or when a power greater than a threshold power is applied to the heater). For example, a duty cycle may be defined by the equation Duty Cycle=PW/T×100%, where PW is the pulse width (e.g., the time during which the heater is turned ON) and T is the period of the entire ON/OFF cycle.

Referencing FIG. 3A, a cryogenic device 100 may attempt to maintain a relatively constant temperature (e.g., 30° C.) on the exterior of the cryogen cartridge 130. A relatively constant, relatively low amount of heat is added throughout a period of use (e.g., by employing a constant, relatively low duty cycle). This approach would work if the temperature at the exterior of the cryogen cartridge 130 reflected the temperature of the cryogen within. However, temperature applied to the exterior of the cryogen cartridge 130 is not transferred to the cryogen within sufficiently quickly, such that the temperature of the exterior of the cryogen cartridge 130 is not an adequate estimate of the temperature of the cryogen within. As borne out by experiments, there is a significant lag in between the heating of the exterior of the cryogen cartridge 130 and the heating of the cryogen within. As such, while the addition of a constant, relatively low amount of heat increases temperature and pressure over time, this increase occurs at a relatively slow rate. As illustrated in FIG. 3A, this rate of increase may not be sufficient to counter the decrease of temperature and pressure caused by the release of cryogenic during the cooling phase 310. As such, in addition to the initial pressure drop corresponding to the bracket 312-1, a continued drop in pressure may be observed during the cooling phase 310, as illustrated by the downward-sloping pressure curve corresponding to the bracket 312-2. The continued drop illustrated in FIG. 3A may be problematic, because this continuous variation in pressure during the cooling phase 310 may translate to variations in cryogen flow rate over the cooling phase 310, and may result in suboptimal cryozone formation. For example, cryogen flow rate may continuously decrease during the cooling phase 310 as pressure continuously decreases, resulting in decreased levels of cooling over the cooling phase 310. As such, a method of maintaining a constant pressure during the cooling phase 310 may be desirable to effectuate consistent cooling during the cooling phase 310 to form a cryozone having desired characteristics (e.g., with a desired volume and temperature profile). Example methods that may be employed to maintain constant pressure during the cooling phase 310 are described herein.

Moreover, in some embodiments, multiple treatment cycles may be necessary for many cryotherapy treatments, for example, to apply an optimal amount of cryotherapy to a target tissue (e.g., a nerve) while minimizing collateral damage (e.g., to surrounding tissue). Alternatively or additionally, multiple treatment cycles may be useful for creating a "treatment line," which may be, for example, a line of treatment spots transverse to an expected location of a target nerve. More information about treatment lines may be found in U.S. Pat. No. 9,295,512 filed Sep. 12, 2013, the full disclosure of which is incorporated herein by reference in their entirety for all purposes. A further requirement for multiple treatment cycles is that following a first treatment cycle, cryogen pressure must recover back to a baseline pressure value prior to initiating a second treatment cycle. In some embodiments, this pressure recovery may occur during a recovery phase that is separate from the cooling phase (e.g., referencing the example of FIG. 3A, the recovery phase 320, which occurs immediately after the cooling phase 310). Pressure recovery is essential to ensure consistent treatment during repeated treatment cycles. As discussed above, variations in pressure affect characteristics of the cryozone that forms during a treatment cycle, and starting a second treatment cycle with a pressure value that is different from the baseline pressure value would result in creating a cryozone during the second treatment cycle that is different from the cryozone created during the first treatment cycle. For example, the second treatment cycle may have started with a pressure value below the baseline pressure value, in which case the flow rate may have been reduced, ultimately resulting in a smaller cryozone than the one formed in the first treatment cycle. This lack of consistency may in some cases render the cryotherapy suboptimal. A continued lack of appropriate pressure recovery during repeated cycles may compound the problem. For example, if pressure keeps dropping between cycles, the cryozones of each treatment cycle may become increasingly smaller. As such, a cryogenic device 100 may use the recovery phase 320 to build internal pressure back up to the baseline pressure value. For example, as illustrated in FIG. 3A, as cryogen flow is halted at the end of the cooling phase 310, pressure starts to increase and continues to do so over the recovery phase 320. In the example of FIG. 3A, where a relatively constant low level of heat is added (e.g., just enough heat to maintain the exterior of the cryogen cartridge 130 at a temperature of approximately 30° C.), this increase in pressure occurs at a relatively low rate, taking place over more than 300 seconds. The pressure increase is constrained by the rate of heat diffusion through the cryogen, which is dependent on the heat differential between a relatively hot area and a relatively cold area. All else equal, a higher heat differential translates to a faster rate of heat diffusion. In the example of FIG. 3A, the relatively low level of heat applied to the exterior of the cryogen cartridge 130 may result in a relatively low heat differential, which in turn translates to a relatively low rate of heat diffusion such that temperature (and thus, pressure) increases relatively slowly. In order to allow for full pressure recovery, the recovery phase 320 needs to be extended to a relatively long period, thereby placing a limit on the rate at which multiple cycles can be performed.

Figure 3B:
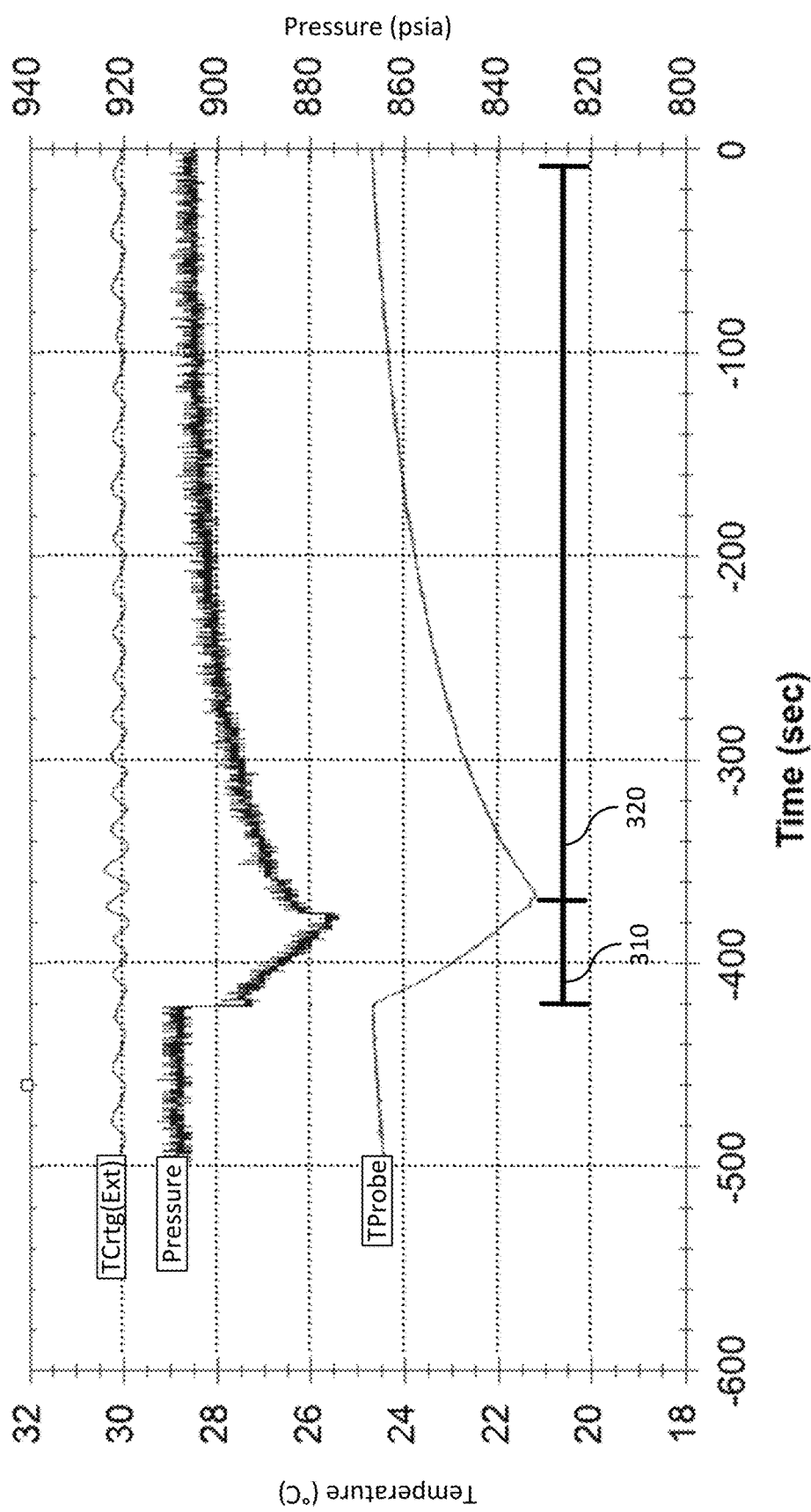
FIG. 3B illustrates an example graph reflecting pressure and temperature within the cryogenic device during a treatment cycle that occurred after the treatment cycle illustrated in FIG. 3A.

FIG. 3B illustrates an example pressure/temperature curve reflecting pressure and temperature within the cryogenic device 100 during a treatment cycle that occurred after the treatment cycle illustrated in FIG. 3A. Like FIG. 3A, FIG. 3B illustrates an approach that attempts to maintain a relatively constant temperature (e.g., 30° C.) on the exterior of the cryogen cartridge 130 by applying a relatively constant, relatively low amount of heat throughout a period of use (e.g., by employing a constant, relatively low duty cycle). FIG. 3B is different from FIG. 3A in that, as described above, the starting pressure was not able to recover back to the original baseline pressure value. This is because the heat added to maintain the temperature of the exterior of the cryogen cartridge 130 at approximately 30° C. may not be sufficient to offset pressure losses from previous cycles. Although the pressure may have recovered given enough time (when cryogen temperature matches the temperature the exterior of the cryogen cartridge 130, e.g., 30° C.), treatment cycles occurring in relatively rapid succession may not allow for sufficient time. As such, the flow rate during the treatment cycle depicted in FIG. 3B may be suboptimal. Furthermore, since the starting pressure is already relatively low, the gap between the actual pressure value and a target pressure value during the cooling phase is expected to widen further during the next treatment cycle since even more heat would be needed in the next treatment cycle to get cryogen pressure to a target pressure value.

Figure 4:
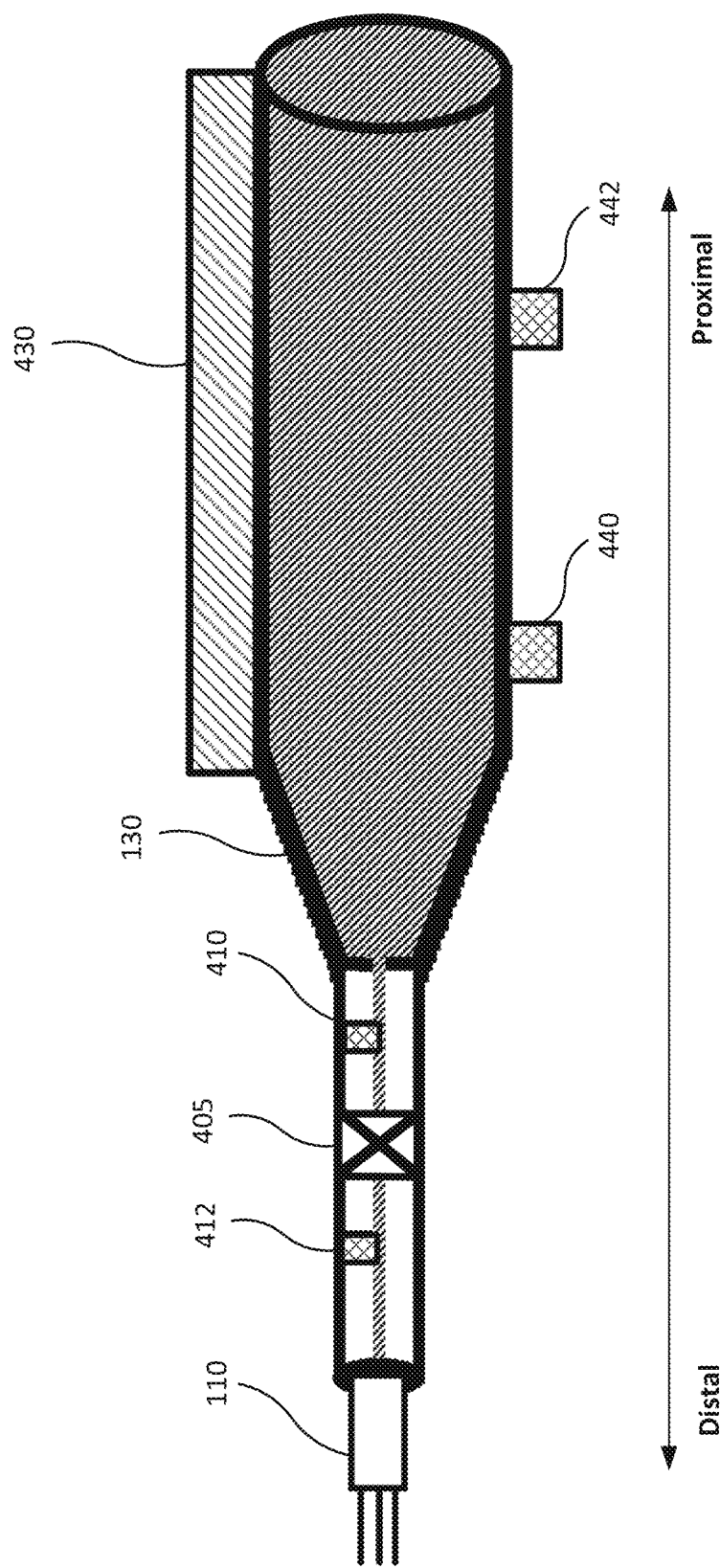
FIG. 4 illustrates a simplified cross-section schematic of an example cryogen cartridge coupled to a needle probe via a cryogen pathway.

FIG. 4 illustrates a simplified cross-section schematic of an example cryogen cartridge 130 coupled to a needle probe 110 via a cryogen pathway. In some embodiments, a heater may be coupled to the cryogen cartridge 130 so as to heat the cryogen within the cryogen cartridge 130. In the example illustrated in FIG. 4, a heater 430 is disposed adjacent to or near the cryogen cartridge 130. In some embodiments, one or more temperature sensors (e.g., the temperature sensors 440 and 442) may be disposed adjacent to or near the cryogen cartridge 130 so as to measure a temperature at the exterior of the cryogen cartridge 130 to approximate temperature within the cryogen cartridge 130. In some embodiments, a supply valve 405 may be disposed along the cryogen pathway to control flow of the cryogen. For example, the supply valve 405 may be made to alternate between an open position and a closed position to allow or prevent cryogen flow downstream toward the needle probe 110. In some embodiments, cryogen flow may be modulated by opening the supply valve to positions in between the open position and the closed position. In some embodiments, one or more pressure sensors (e.g., the upstream pressure sensor 410 and the downstream pressure sensor 412) may be disposed along the cryogen pathway to monitor cryogen pressure. Although the simplified schematic of FIG. 4 illustrates a particular configuration and number of particular elements (e.g., the heater 430, the temperature sensors 440 and 442, the pressure sensors 410 and 412) disposed in particular locations, this disclosure contemplates that any number and configuration of these elements may be disposed in any suitable location. For example, the heater 430 may be positioned near but not immediately adjacent to the cryogen cartridge. As another example, a second heater may be positioned adjacent to the cryogen cartridge 130. As another example, the cryogenic device 100 may include only a single pressure sensor (e.g., the upstream pressure sensor 410).

In some embodiments, a probe descriptor may be transmitted by a first needle probe 110 that includes a first flow rate value that corresponds to an expected average mass flow rate of a cryogen through the first needle probe 110 of the cryogenic device 100 during a cryotherapy treatment cycle. A processor of the cryogenic device 100 (e.g., a first processor located on a handpiece portion of the cryogenic device 100) may receive this first flow rate value. In some embodiments, the processor of the cryogenic device 100 may use the first flow rate value to determine an amount of cryogen that is flowed to needles of the needle probe 110 during a particular treatment cycle. For example, the first flow rate value may correspond to an expected average mass flow rate of n. In this example, if a particular treatment cycle includes a cooling phase with a duration of 20 seconds, the processor may calculate that 20n units of cryogen have been flowed to the needles of the needle probe 110 during the particular treatment cycle. In some embodiments, each individual needle probe 110 may include (e.g., as part of an associated probe descriptor), information about its respective flow rate value, and may transmit that flow rate value (e.g., as part of its probe descriptor) to a processor of the cryogenic device 100. For example, the first needle probe 110 may be replaced by a second needle probe 110. At some point (e.g., immediately after insertion of the second needle probe 110 into the probe receptacle 170, after receipt of an input to begin a treatment cycle, etc.), the second needle probe 110 may transmit its own flow rate value to the processor of the cryogenic device 100 for processing. In some embodiments, each needle probe 110 may have probe descriptors that include information about prescribed parameters relating to delivery cycle timing. For example, a probe descriptor for a particular needle probe 110 may include information about a pre-heat time (e.g., during which a skin warmer of the cryogenic device 100 may be heated so as to reduce collateral damage to the skin as described above), cooling phase duration (e.g., during which the valve is to remain open), recovery phase duration (e.g., during which the valve is to be closed), and/or any other suitable parameters. In this example, each of these parameters may be uniquely tailored to the specifics of the needle probe 110. For example, the cooling phase duration for a five-needle probe may be less than the cooling phase duration for a three-needle probe.

In some embodiments, the flow rate value of a needle probe 110 may be used by the processor of the cryogenic device 100 to calculate an amount of cryogen that has been used and/or an amount that is remaining in the cryogen cartridge 130. The processor of the cryogenic device 100 may calculate these amounts based on the average mass flow rate and the amount of time a supply valve for releasing cryogen has been opened. In some embodiments, the flow rate value may be derived from needle dimensions, the number of needles, and/or other suitable parameters associated with the needle probe 110. In some embodiments, the flow rate value may be empirically determined through testing. For example, particular probe types may be tested to determine average flow rate values for each probe type. As another example, each particular needle probe 110 may be tested individually and an individualized flow rate value may be determined and assigned to the particular needle probe 110, such that the probe descriptor transmitted by the particular needle probe 110 includes the individualized flow rate value. Such individualized flow rate values may be especially useful in cases where it is infeasible to have tight tolerances in manufacturing (such that even two different needle probes of a single type may have varying flow rates, e.g., because of varying dimensions in their respective lumens due to variances in manufacturing).

Figure 5:
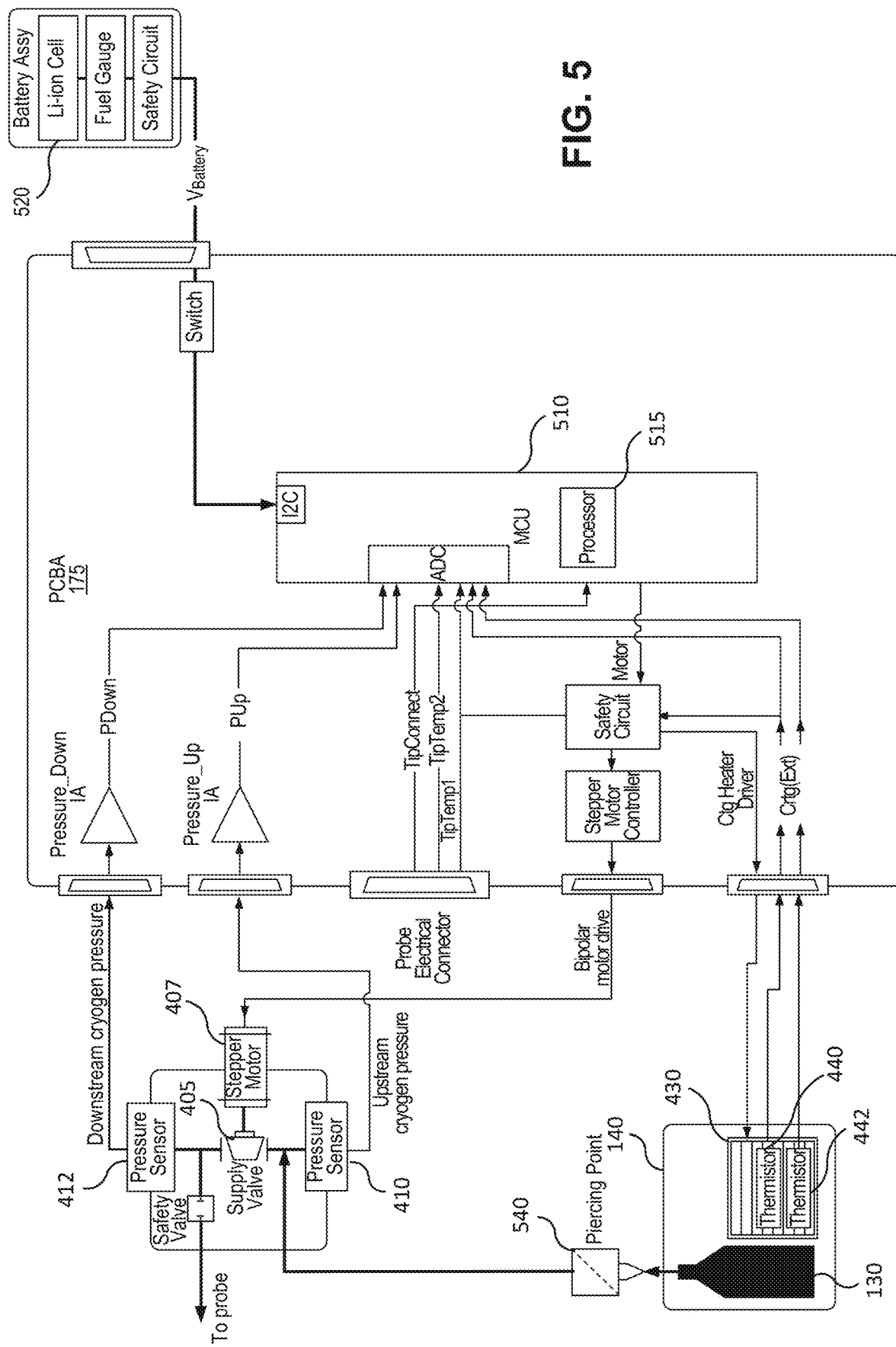
FIG. 5 illustrates an example high-level system diagram of a cryogenic device.

FIG. 5 illustrates an example high-level system diagram of a cryogenic device 100. FIG. 5 illustrates the PCBA 175 of the cryogenic device 100 along with other elements that interface with the PCBA 175. In some embodiments, referencing FIG. 5, a piercing element 540 may be housed within the cryogenic device, in a position so as to pierce the cryogen cartridge 130 using a piercing point. Once the cryogen cartridge 130 is pierced, the pressurized cryogen within may be fluidically coupled to the cryogen pathway leading to the needle probe 110 via a cryogen pathway that extends through the piercing element 540 and toward the supply valve 405 that may control cryogen flow from the cryogen cartridge 130 to the needle probe 110. In some embodiments, the cryogenic device 100 may include an upstream pressure sensor 410 for measuring pressure upstream from the supply valve 405 and a downstream pressure sensor 412 for measuring pressure downstream from the supply valve 405. The supply valve 405 may be opened or closed by any suitable means. For example, a stepper motor 407 (e.g., controllable via the microcontroller unit 510) may be used to move the valve between an open position and a closed position, or a position therebetween. Typically, when the supply valve 405 is fully open during a cooling phase of a treatment cycle, the upstream pressure is approximately equal to the downstream pressure. As such, some embodiments of the cryogenic device 100 may include only the upstream pressure sensor 410, which approximates the pressure within the cryogen cartridge 130 when it is fluidically coupled to the cryogen pathway (e.g., after the cryogen cartridge 130 is pierced by the piercing point 540). Other embodiments of the cryogenic device 100 may include both the upstream pressure sensor 410 and the downstream pressure sensor 412, for example, for diagnosing delivery issues (e.g., to determine whether the valve 405 has failed to open or close, or to determine if there is a blockage in between the two pressure sensors 410 and 412).

Referencing FIG. 5, in some embodiments, the cryogenic device 100 may include a microcontroller unit 510 for monitoring and operating the cryogenic device 100. In some embodiments, the cryogenic device 100 may include one or more processors such as the processor 515. The one or more processors 515 may be part of a microcontroller unit 510 disposed on the PCBA 175. In some embodiments, the processor 515 (or any other suitable circuitry) may determine a first target heater power to be applied to a heater 430 associated with the cryogenic device 100 for a first treatment cycle. In some embodiments, the target heater power may be a heater power value that is configured to generate heat via the heater 430 to offset a pressure/heat loss that occurs during a cooling phase of a treatment cycle so as to stabilize pressure within the cryogenic device 100 during the cooling phase. This pressure stabilization may also be optimal for allowing for fast recovery during a recovery phase following the cooling phase, because it may prevent pressure from dropping too low during the cooling phase. The processor of the cryogenic device 100 may transmit a signal instructing circuitry associated with the heater 430 to apply the first target heater power to the heater so as to heat the cryogen. In some embodiments, the processor 515 may determine this first target heater power based on the first flow rate value. In some embodiments, as described above, the cryogenic device 100 may theoretically derive an amount of cryogen that is expected to be released from the cryogen cartridge 130 when the first needle probe 110 is in use. For example, it may calculate the amount of expected cryogen released by multiplying the average mass flow rate correlated with the first flow rate value by a duration of cryogen flow (e.g., as may be determined based on a duration of the supply valve 405 being open). In cases where the amount of cryogen released may be modulated at the supply valve 405 (e.g., opening the valve by 30%, 50%, etc.), the calculation may be appropriately weighted to account for this modulation. The cryogenic device 100 may then use the amount of cryogen released to estimate a target energy amount required to compensate for heat lost by the cryogen release. A target heating power may then be derived (e.g., by dividing the target energy amount by an amount of time a cooling phase is expected to take). This derived heating power may be applied to the heater 430 to increase pressure of cryogen within the cryogenic device 100 so as to stabilize pressure during the cooling phase and/or allow pressure recovery during a recovery phase. In some embodiments, the target heating power (or the amount of heat required) may be, alternatively or additionally, empirically derived. For example, flow rate values may be correlated with amounts of expected cryogen release, or with target heating powers (or amounts of heat required). In this example, a processor of the cryogenic device 100 may access a lookup table to determine a target heating power, or alternatively may use an empirically derived mathematical model or function to determine the target heating power. The cryogenic device 100 may also include one or more temperature sensors (e.g., thermistors) 440 and 442, which may be used to measure the temperature of the exterior of the cartridge (e.g., referencing FIGS. 3A-3B, reflected by the curve labeled TCrtg(Ext)). Temperature signals corresponding to the measured temperatures may be transmitted to the microcontroller unit 510.

In some embodiments, the processor 515 of the cryogenic device 100 may receive an input for the first treatment cycle. For example, a user may actuate an input button that causes an input signal to be communicated to the processor 515 of the cryogenic device 100. In response to the input, the processor 515 of the cryogenic device 100 may cause the cryogen to flow for a period of time (e.g., by causing the supply valve 405 to open) toward the first needle probe 110, the period of time corresponding to the cooling phase of a treatment cycle.

Figure 6:
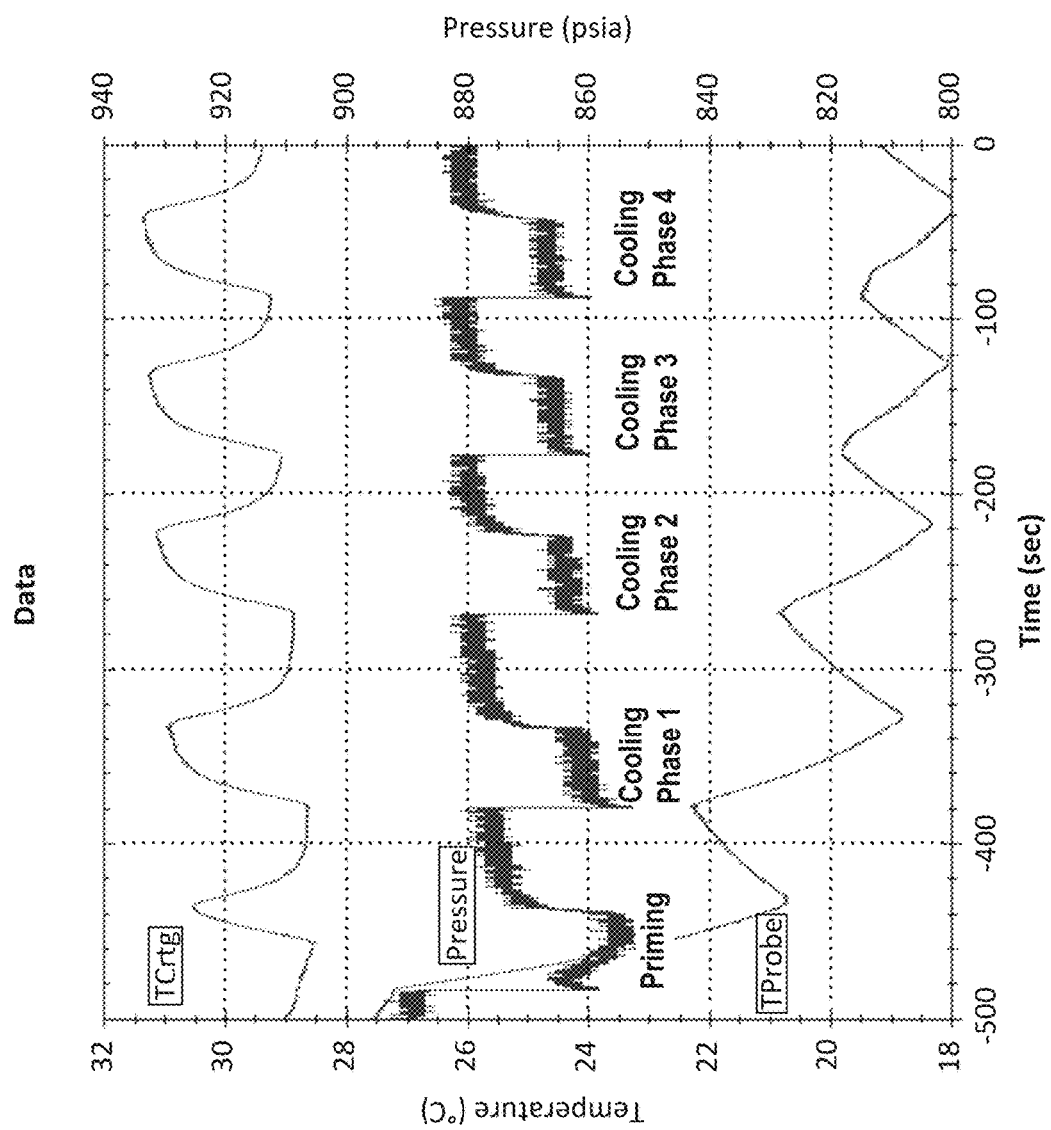
FIG. 6 illustrates an example pressure/temperature graph corresponding to a method of stabilizing cryogen pressure by applying a target heater power intended specifically to offset the amount of pressure lost during cooling phases of treatment cycles.

FIG. 6 illustrates an example pressure/temperature graph corresponding to a method of stabilizing cryogen pressure by applying a target heater power intended specifically to offset the amount of pressure lost during cooling phases of treatment cycles. FIG. 6 illustrates a priming cycle followed by four treatment cycles with cooling phases 1 to 4. The approach illustrated in FIG. 6 may be used to maintain relatively constant pressures during cooling phases as cryogen is delivered. As described in further detail below, such an approach has several advantages. In some embodiments, the processor 515 of the cryogenic device 100 may cause the heater to apply the first target heater power during the first treatment cycle so as to heat the cryogen and stabilize pressure within the cryogenic device prior to, during, or after the first treatment cycle. The first target heater power may be applied over a period of time (e.g., during a cooling phase of a first treatment cycle) by any suitable means. In some embodiments, circuitry associated with the heater may be made to vary a voltage or current supplied to the heater. In other embodiments, the heater may be supplied with constant voltage and current, but the heater power ultimately applied by the heater during a period of time may be varied by varying a duty cycle of the heater. In these embodiments, the following equation may be used to determine an appropriate duty cycle for applying a target heater power: Duty Cycle=$P_{Target} \times (R_{Heater}/V_{Heater}^2)$, wherein $P_{Target}$ is the first target heater power, $R_{Heater}$ is the resistance of the heater, and $V_{Heater}$ is the voltage across the heater. Pressure stabilization may involve maintaining an average rate of change in pressure within a predetermined range (or maintaining pressure relatively constant) during a cooling phase of a treatment cycle. Referencing FIG. 6, a target heater power is applied to cartridge so as to keep the pressure within each cooling phase relatively constant. As illustrated by the TCrtg(Ext) line in the example of FIG. 6, heater power is no longer applied to keep temperature at the cartridge exterior at a constant 30° C. Rather, in this example, a relatively high heater power may be applied to rapidly raise cryogen temperature during the cooling phases to specifically offset estimated pressure losses during the cooling phases. For example, the heater may be operated with a duty cycle of approximately 23%, with the heater turned ON during cooling phases to offset the estimated pressure losses. The relatively high heater power is able to more quickly transfer heat to (and thus increase pressure of) cryogen within the cryogen cartridge 130, when compared to lower duty cycles that would otherwise be employed to maintain the cartridge exterior at a constant temperature (e.g., around 30° C.).

By applying a target heater power specifically tailored to offsetting pressure losses during cooling phases, cryogen pressure may be stabilized during the cooling phases so as to allow for consistent cryogen flow during cooling phases. As illustrated by the relatively flat pressure lines during Cooling Phases 1 to 4 in FIG. 6, pressure is kept relatively constant during the cooling phases. This constant pressure during the cooling phases in turn allows for consistent application of cooling energy during the cooling phases, ultimately resulting in optimal cryozone formations.

Another advantage of this tailored approach (as compared to the more conventional approaches that simply maintain constant temperatures of the exterior of the cryogen cartridge 130) is that the recovery phase is shortened, thereby allowing for the performance of multiple treatment cycles over a shorter period of time. This shortened recovery phase may be due to the fact that a continued drop in pressure does not occur during the cooling phase. For example, referencing FIG. 3A (in which a heater is engaged to keep temperature at the exterior of the quote incorporate 130 constant), after an initial pressure drop at the beginning of the cooling phase, pressure continues to drop over the cooling phase. By contrast, referencing FIG. 6 (in which a heater applies a relatively high target heater power specifically tailored to offset pressure losses), after an initial pressure drop at the beginning of the cooling phase, pressure is stabilized during the remainder of the cooling phase. As such, at the end of a cooling phase, the overall pressure drop in the approach illustrated in FIG. 6, as compared to its baseline pressure value, is less than the overall pressure drop in the approach illustrated in FIG. 3A as compared to its baseline pressure value. The smaller difference in pressure (i.e., between the pressure at the end of the cooling phase and the baseline pressure value) means that, all else equal, less time would be required to bring pressure back up to the baseline pressure value. Additionally, the approach illustrated in FIG. 6 applies a higher heater power relative to the approach illustrated in FIG. 3A, and as such, allows for faster heat transfer to the cryogen as discussed above. As such, pressure may be brought back to the baseline pressure value at a faster rate as the cryogen is caused to be heated more quickly.

Figure 7:
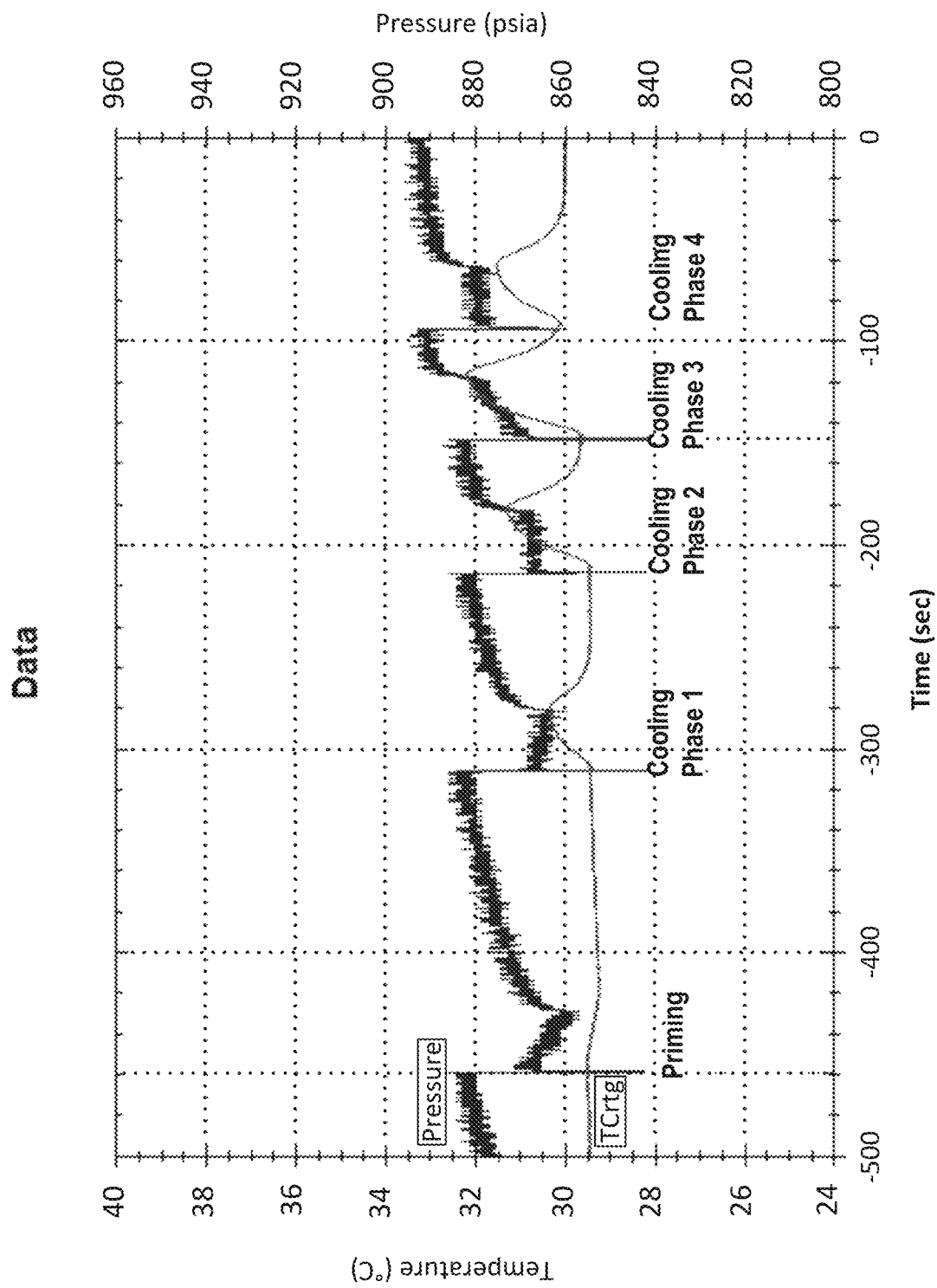
FIG. 7 illustrates an example pressure/temperature graph corresponding to a method of real-time pressure monitoring and correction for stabilizing pressure during cooling phases.

FIG. 7 illustrates an example pressure/temperature graph corresponding to a method of real-time pressure monitoring and correction for stabilizing pressure during cooling phases. By using pressure measurements to directly determine the pressure of the cryogen within the cryogen cartridge 130, accurate real-time pressure may be determined. This is in contrast to the more conventional approaches that use temperature measurements taken at the exterior of the cryogen cartridge 130. As such, pressure can be monitored and adjusted in real-time to adjust for any deviations from expected pressure values when applying an initially determined target heater power. For example, while a first target heater power may be a good theoretical estimate as to the amount of heat that needs to be added to offset pressure drops during a cooling phase, real-world factors may cause this estimate to be inaccurate. For example, manufacturing deviations may result in variations in heater resistance (causing deviations in the amount of heat applied when a specified heater power is applied), supply tube dimensions (causing deviations in cryogen flow rates from an expected flow rate as estimated using an associated flow rate value). Some of these manufacturing deviations can be mitigated by individualized testing of the cryogenic device 100 (e.g., testing each needle probe individually and then specifying an individualized flow rate value for the needle probe as described above) and/or running a calibration routine to account for the deviations. However, such testing and/or calibration may not always be feasible, and there may be factors that are not easily tested for or calibrated. As such, real-time monitoring and correction may be advantageous. FIG. 7 illustrates an example where following a priming cycle, a first target heater power is applied during Cooling Phase 1 in an attempt to stabilize pressure during Cooling Phase 1. However, the cryogenic device 100 may determine that this first target heater power was insufficient to maintain a constant average pressure during Cooling Phase 1, e.g., as evidenced by the negative slope during Cooling Phase 1, indicating a continued drop in pressure during Cooling Phase 1. For example, the processor 515 of the cryogenic device 100 may receive pressure data from a pressure sensor of the cryogenic device during Cooling Phase 1 and may calculate an average rate of change in pressure during Cooling Phase 1. In an attempt to stabilize pressure so that average pressure remains constant during the next cooling phase (i.e., Cooling Phase 2), the cryogenic device 100 may adjust the target heater power upward. The processor 515 may determine that the average rate of change in pressure is negative, and may calculate an adjusted target heater power for Cooling Phase 2, wherein the adjusted target heater power is calculated at least in part by adjusting the first target heater power upward by an adjustment value based on the average rate of change in pressure during Cooling Phase 1. The processor 515 may then cause the heater 430 to apply the adjusted target heater power during Cooling Phase 2 (e.g., by increasing the duty cycle, by increasing a voltage supplied to the heater 430, etc.). This increase in heater power is illustrated by the TCrtg line in FIG. 7, which shows a sharp increase in temperature around the exterior of the cryogen cartridge during Cooling Phase 2, evidencing the increase in heater power. As shown by the relatively flat pressure curve during Cooling Phase 2 in FIG. 7, the increased heater power allowed average pressure to remain constant during Cooling Phase 2.

Similarly, the cryogenic device 100 may adjust heater power to respond to a rate of change in pressure that is positive. For example, Cooling Phase 3 in FIG. 7 illustrates a positive change in pressure, which may have been caused by a heater power that may have been too high. In some embodiments, the processor 515 of the cryogenic device 100, having determined that the average rate of change in pressure during Cooling Phase 3 is positive beyond a predetermined range, and may calculate an adjusted target heater power for the next cooling phase (i.e., Cooling Phase 4). This adjusted target heater power may be calculated, for example, at least in part by adjusting the target heater power that was applied during Cooling Phase 3 downward by an adjustment value. The adjustment value may be based on the average rate of change in pressure that occurred during Cooling phase 3. The processor 515 may then cause the heater 430 to apply the adjusted target heater power during Cooling Phase 4, which may result in a relatively constant average pressure during Cooling Phase 4, as shown by the relatively flat pressure curve in FIG. 7 during Cooling Phase 4. The table below shows example heater power adjustments made during each of the cooling phases illustrated in FIG. 7, as made by adjusting a duty cycle of the heater:

| Cooling Phase | Duty Cycle % |
| --- | --- |
| Priming | 0 |
| 1 | 10 |
| 2 | 20 |
| 3 | 30 |
| 4 | 20 |

In some embodiments, the adjustment value may be determined based on a magnitude of the average rate of change in pressure. For example, a relatively high adjustment value may be determined for a relatively high magnitude, and a relatively low adjustment value may be determined for a relatively low magnitude. In some embodiments, the processor 515 may access a lookup table, or alternatively may use an empirically derived mathematical model or function to determine an appropriate adjustment value. In some embodiments, the effect of a heater power adjustment on the slope of the pressure during delivery may be characterized for each probe type, and the cryogenic device 100 may base heater power adjustments on this characterization, allowing a fairly precise estimate of the appropriate correction to be made for any probe type and measured slope. For example, all else equal, a cryogenic device 100 receiving a probe descriptor indicating that an attached probe is a three-needle probe may calculate a first adjustment value, while a cryogenic device 100 receiving a probe descriptor indicating that an attached probe is a five-needle probe may calculate a second adjustment value that is different from the first adjustment value (e.g., a higher adjustment value may be calculated for the five-needle probe, because the five-needle probe may have a higher average mass flow rate such that a higher heater power adjustment may be needed to effect the same desired change in pressure). As another example, all else equal, a first adjustment value may be calculated for a single-needle probe with a 90 mm needle and a second adjustment value may be calculated for a three-needle probe with 9 mm needles (e.g., a higher adjustment value may be calculated for the single-needle 90 mm probe, because the single-needle 90 mm probe may have a higher average mass flow rate than the three-needle 9 mm probe). In other embodiments, the cryogenic device 100 may apply coarse adjustments (e.g., 10% duty cycle increments) if the average rate of change in pressure during cooling phase exceeds some pre-determined threshold, and finer increments (e.g., 2% duty cycle increments) for an average rate of change in pressure less than this pre-determined threshold. Such an approach could be extended to multiple thresholds with additional adjustment increments (e.g., a higher threshold, above which pressure is adjusted in 20% duty cycle increments).

In some embodiments, target heater power may be adjusted based on values of pressure prior to a cooling phase. For example, if it is determined that the pressure value prior to a particular cooling phase is below an optimal baseline pressure value, the cryogenic device 100 may accordingly adjust upward a target heater power to be delivered during the particular cooling phase. As another example, if it is determined that the pressure value prior to a particular cooling phase is above an optimal baseline pressure value, the cryogenic device 100 may accordingly adjust downward a target heater power to be delivered during the particular cooling phase. This type of monitoring and adjustment may be desirable in that it provides a macro-level stabilization that can address falling baseline levels that may have compounded over the course of multiple treatment cycles.

In some embodiments, target heater power may be adjusted based on a comparison of values of pressure prior to and following a cooling phase. For example, the cryogenic device may determine a first pressure of the cryogenic device 100 immediately prior to a cooling cycle of a first treatment cycle, and a second pressure of the cryogenic device 100 immediately prior to a cooling cycle of a second, subsequent treatment cycle. In this example, the cryogenic device 100 may then calculate a second target heater power for the second treatment cycle, wherein the second target heater power is calculated at least in part by adjusting the first target heater power upward or downward based on a determined difference between the first pressure the second pressure. For example, when the second pressure is lower than the first pressure, a target heater power may be adjusted upward. As another example, when the second pressure is greater than the first pressure, a target heater power may be adjusted downward.

In some embodiments, the cryogenic device 100 may also monitor the voltage of a power source of the cryogenic device 100 during use. In some embodiments, this voltage may serve as an estimate for voltage across the heater 430 and may therefore be used to ensure that the heater 430 is accurately delivering a specified target heater power. For example, referencing FIG. 5, the microcontroller unit 510 of the cryogenic device 100 may receive signals from a battery 520 (e.g., a lithium-ion battery cell) indicating a voltage ($V_{Battery}$) of the battery 520. In this example, $V_{Battery}$ may be inserted as $V_{Heater}$ into, for example, the equation for calculating the duty cycle as described above, i.e., Duty Cycle=$P_{Target} \times (R_{Heater}/V_{Heater}^2)$. Battery voltage may vary over time due to a variety of factors, such as the amount of charge remaining in the battery. For example, battery voltage may vary between 4.2 V and 3.2 V, depending on the charge remaining. Even a small variance in battery voltage may have a significant impact in the duty cycle calculation, because $V_{Heater}$ is squared. As such, calculating duty cycle with updated estimates of $V_{Heater}$ may help ensure that appropriate duty cycles are employed and thereby reduce the likelihood of pressure swings due to incorrect duty cycle calculations. In some embodiments, the cryogenic device 100 may alternatively monitor the current of the power source, which may be used to derive $V_{Heater}$.

Figure 8:
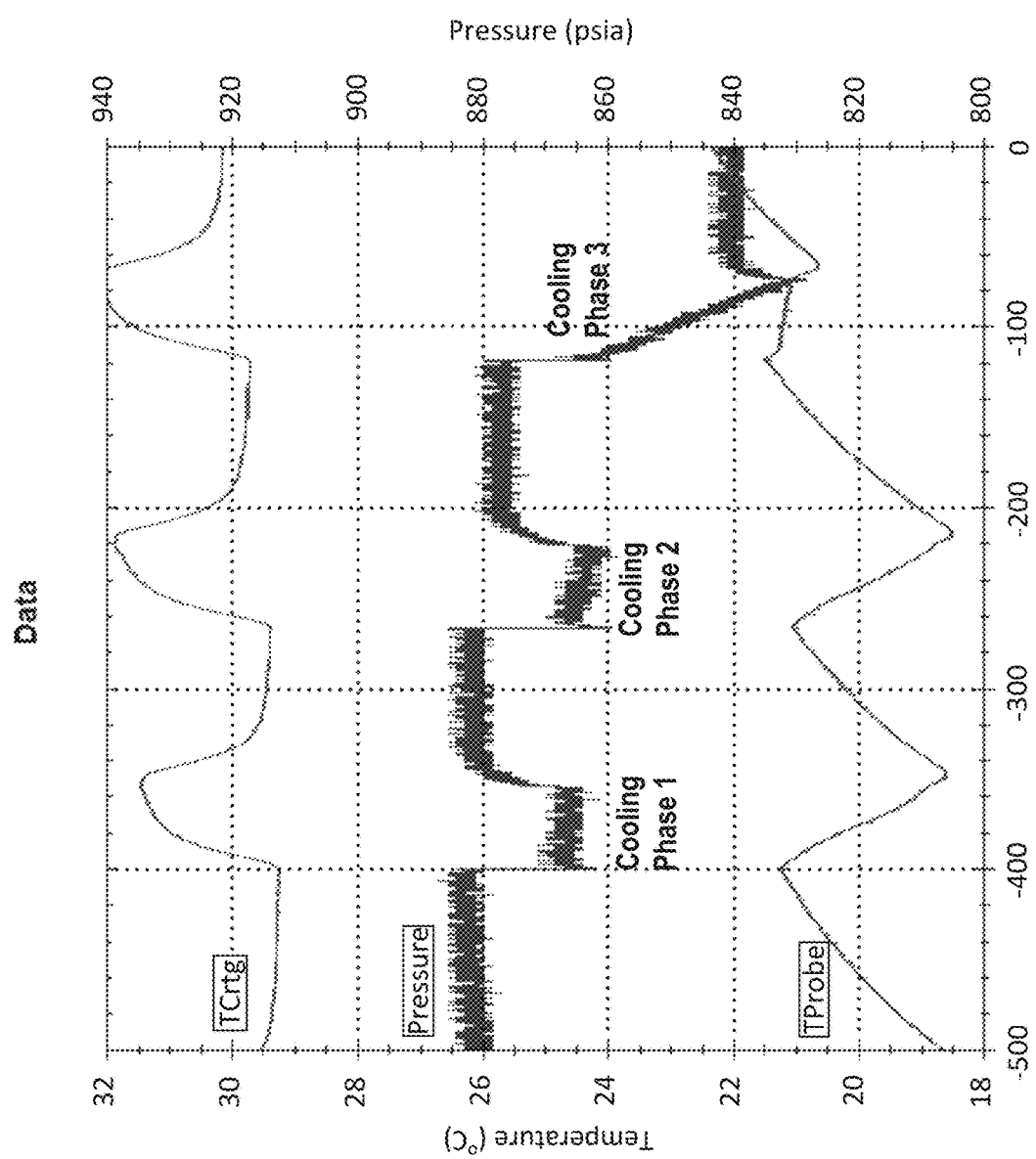
FIG. 8 illustrates an example pressure/temperature graph of multiple treatment cycles, including a treatment cycle indicating an issue with the cryogenic device.

FIG. 8 illustrates an example pressure/temperature graph of multiple treatment cycles, including a treatment cycle indicating an issue with the cryogenic device 100. In some embodiments, the cryogenic device 100 may use pressure measurements as a means for spotting issues with the cryogenic device 100. In some embodiments, an average rate of change in pressure (or an overall change in pressure) that is greater than an expected average rate of change in pressure (or an expected overall change in pressure) may indicate an issue with the cryogenic device 100 that may require an action more than simply adjusting a heater power as described above. For example, if the change in pressure exceeds the expected change in pressure by a threshold magnitude (or if a rate of change in pressure exceeds an expected rate of change in pressure), the cryogenic device 100 may determine that there is an issue with the cryogenic device 100. Referencing FIG. 8, for example, when an average rate of change in pressure (e.g., during a cooling phase) is negative beyond a threshold magnitude rate (e.g., as shown by the large negative slope during Cooling Phase 3), the cryogenic device 100 may determine that the amount of cryogen within the cryogen cartridge 130 may be critically depleted. This rate of change in pressure beyond the threshold magnitude rate may be a reflection of a lack of cryogen in the system to allow for sufficient buildup of pressure. Additionally or alternatively, the cryogenic device 100 may determine that the same issue may exist if pressure does not recover back to a baseline pressure value after a recovery phase following a cooling phase (e.g., referencing FIG. 8, the recovery phase after Cooling Phase 3). As another example, when an average rate of change in pressure is positive beyond a threshold magnitude rate as compared to an expected rate of change in pressure, the cryogenic device 100 may determine that an issue with cryogen delivery may exist (e.g., a blocked or impeded cryogen pathway, an issue with the supply valve 405). In these cases, a processor (e.g., the processor 515) of the cryogenic device 100 may in some embodiments generate a notification indicating an issue with the cryogenic device. In some embodiments, the notification may identify the particular issue that the cryogenic device 100 determines to be likely. In some embodiments, the notification may be caused to be displayed on a display device (e.g., a screen disposed on the cryogenic device 100, a screen of an external device, etc.).

Figure 9:
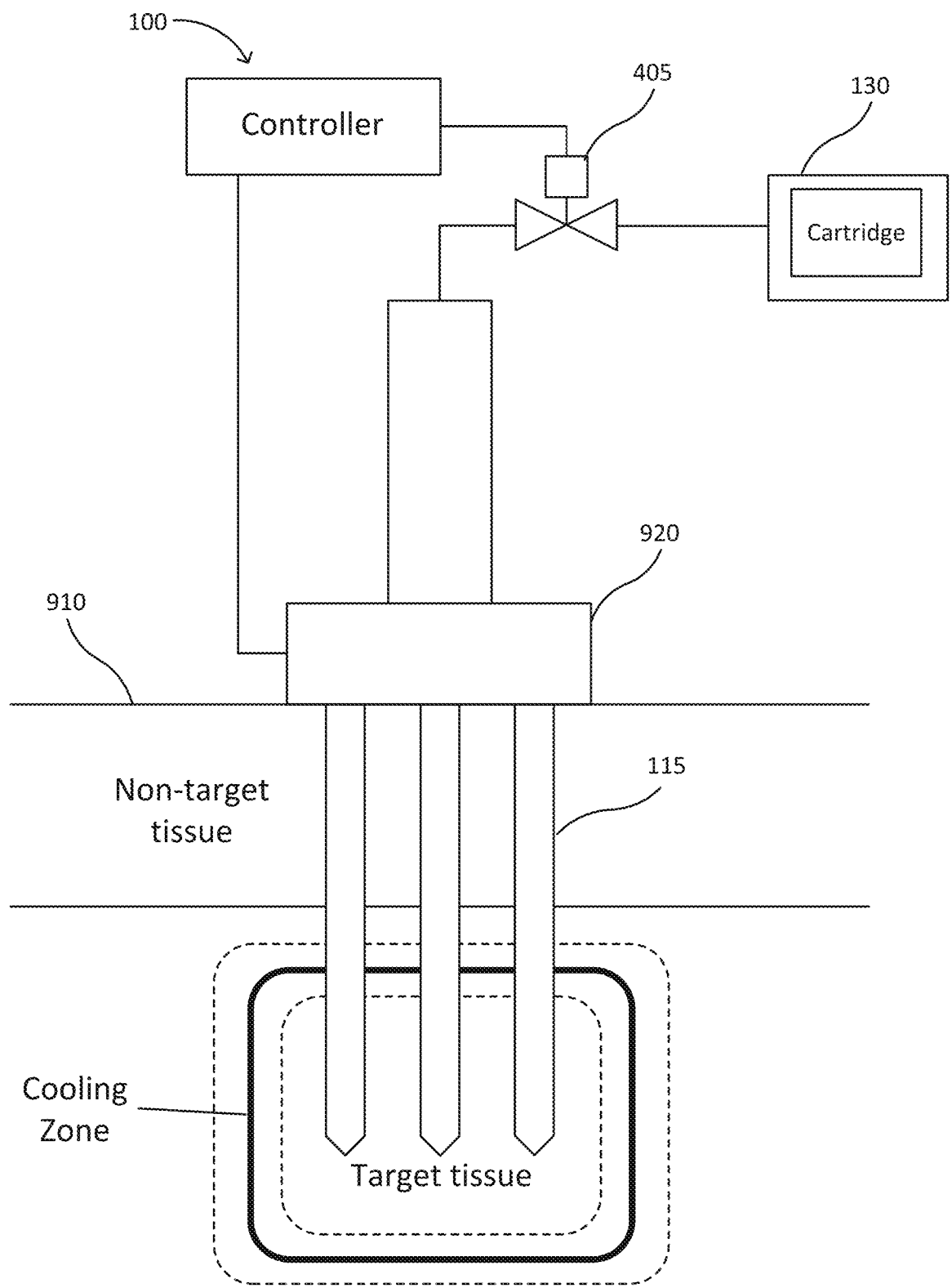
FIG. 9 illustrates a simplified schematic diagram of a cryogenic device while in use.

FIG. 9 illustrates a simplified schematic diagram of a cryogenic device 100 while in use. As illustrated, the needles 115 of a needle probe may be inserted into and beyond the skin 810 of the patient such that distal portions of the needles 115 are adjacent to a target tissue (e.g., nerve tissue). In some embodiments, an operator may select a needle probe such that the needles 115 are sized so as to extend distally beyond non-target tissue and adjacent to a target tissue when a tissue-engaging surface 920 is made to contact the skin 910. In some embodiments, once the needles 115 are positioned, an operator may submit an input to the cryogenic device 100 (e.g., by actuating a button, tapping a user interface element on a touchscreen, etc.) to cause a controller to open a supply valve 405, thereby enabling a cryogen to flow from the cartridge 130 to the lumens of the needles 115 via a cryogen pathway. The needles 115 may be configured such that distal portions of the needles 115 are cooled more than proximal portions of the needles 115. As such, the distal portions of the needles 115 may create a cooling zone around the target tissue as illustrated in FIG. 9.

Figure 10:
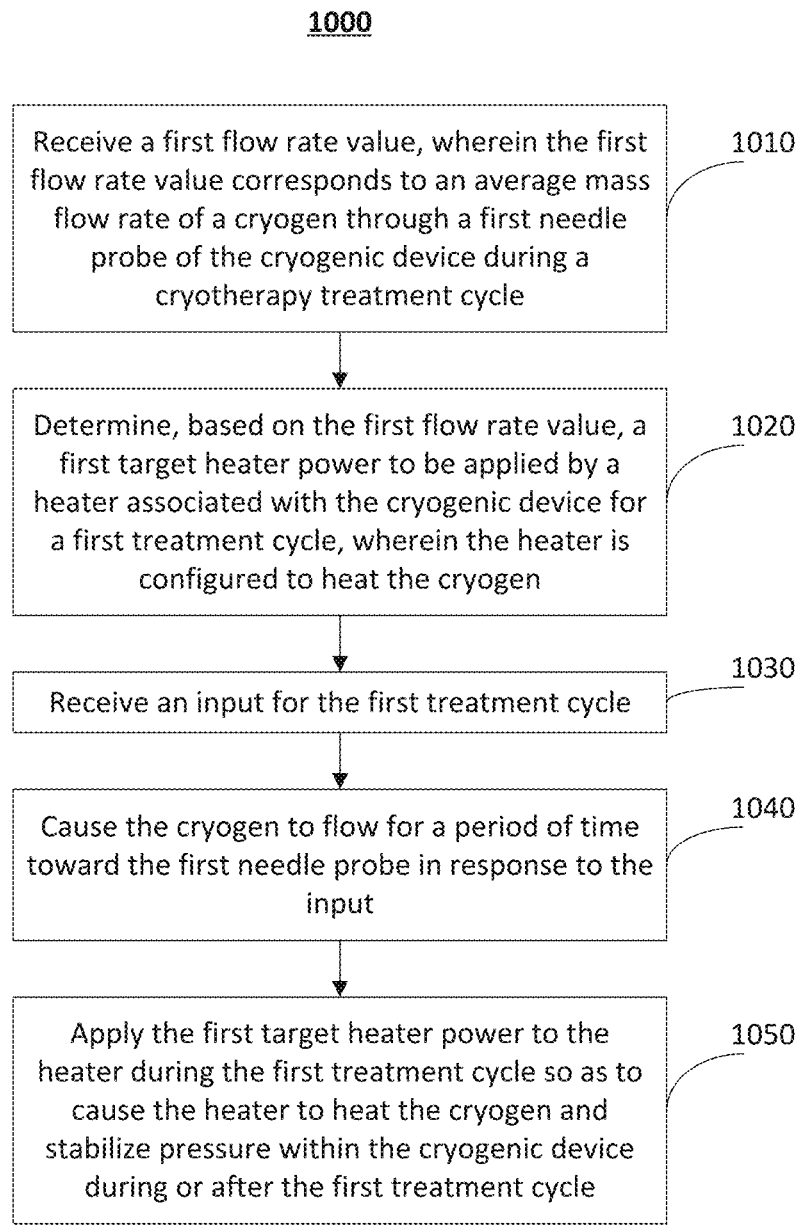
FIG. 10 illustrates an example method for stabilizing pressure within a cryogenic device.

FIG. 10 illustrates an example method 1000 for stabilizing pressure within a cryogenic device. The method may include, at step 1010, receiving a first flow rate value, wherein the first flow rate value corresponds to an expected average mass flow rate of a cryogen through a first needle probe of the cryogenic device during a cryotherapy treatment cycle. At step 1020, the method may include determining, based on the first flow rate value, a first target heater power to be applied to a heater associated with the cryogenic device for a first treatment cycle, wherein the heater is configured to heat the cryogen. At step 1030, the method may include receiving an input for the first treatment cycle. At step 1040, the method may include causing the cryogen to flow for a period of time toward the first needle probe in response to the input. At step 1050, the method may include applying the first target heater power to the heater during the first treatment cycle so as to heat the cryogen and stabilize pressure within the cryogenic device during or after the first treatment cycle. Particular embodiments may repeat one or more steps of the method of FIG. 10, where appropriate, and may include additional or varied steps as appropriate. For example, as described in further detail above, heater power may be adjusted for successive treatment cycles and the adjusted heater power may be applied during a following second treatment cycle (e.g., if it is determined that the first heater power resulted in an average negative rate of change in pressure during a cooling phase of the first treatment cycle that is below a predetermined range, a second target heater power may be calculated for the second treatment cycle by adjusting the first heater power upward). Although this disclosure describes and illustrates particular steps of the method of FIG. 10 as occurring in a particular order, this disclosure contemplates any suitable steps of the method of FIG. 10 occurring in any suitable order. Moreover, although this disclosure describes and illustrates an example method for stabilizing pressure within a cryogenic device, including the particular steps of the method of FIG. 10, this disclosure contemplates any suitable method for stabilizing pressure within a cryogenic device, including any suitable steps, which may include all, some, or none of the steps of the method of FIG. 10, where appropriate. Furthermore, although this disclosure describes and illustrates particular components, devices, or systems carrying out particular steps of the method of FIG. 10, this disclosure contemplates any suitable combination of any suitable components, devices, or systems carrying out any suitable steps of the method of FIG. 10.

While the exemplary embodiments have been described in some detail for clarity of understanding and by way of example, a number of modifications, changes, and adaptations may be implemented and/or will be obvious to those as skilled in the art.

What is claimed is:

1. A method for stabilizing pressure within a cryogenic device during a cryotherapy treatment, the method comprising:
   receiving a first flow rate value, wherein the first flow rate value corresponds to an expected average mass flow rate of a cryogen through a first needle probe of the cryogenic device during a cryotherapy treatment cycle;
   determining, based on the first flow rate value, a first target heater power to be applied to a heater associated with the cryogenic device for a first treatment cycle, wherein the heater is configured to heat the cryogen;
   receiving an input for the first treatment cycle;
   causing the cryogen to flow for a period of time toward the first needle probe in response to the input;
   applying the first target heater power to the heater during the first treatment cycle so as to cause the heater to heat the cryogen and stabilize pressure within the cryogenic device during or after the first treatment cycle;
   receiving pressure data from a pressure sensor of the cryogenic device during the first treatment cycle;
   calculating, based on the received pressure data, an average rate of change in pressure during a cooling phase of the first treatment cycle; and
   calculating a second target heater power for a second treatment cycle, wherein the second target heater power is calculated at least in part by adjusting the first target heater power upward or downward by an adjustment value based on the average rate of change in pressure.

2. The method of claim 1, wherein the first target heater power is defined such that an average rate of change in pressure during a cooling phase of the first treatment cycle remains within a predetermined range.

3. The method of claim 1, wherein the first flow rate value is received by a processor of the cryogenic device from the first needle probe.

4. The method of claim 1, wherein the heater is coupled to a cryogen cartridge associated with the cryogenic device, wherein the cryogenic device comprises a handpiece portion, and wherein the cryogen cartridge and the first needle probe are directly coupled to the handpiece portion, a cryogen pathway extending between the cryogen cartridge and the first needle probe.

5. The method of claim 1, further comprising:
   determining a target duty cycle necessary for applying the first target heater power;
   wherein applying the first target heater power engages the heater for the target duty cycle.

6. The method of claim 1, wherein applying the first target heater power comprises adjusting an amount of current or voltage applied to the heater.

7. The method of claim 1, further comprising determining that the average rate of change in pressure is negative and beyond a predetermined range, wherein the second target heater power is calculated at least in part by adjusting the first target heater power upward by the adjustment value.

8. The method of claim 1, further comprising determining that the average rate of change in pressure is positive and beyond a predetermined range, wherein the second target heater power is calculated at least in part by adjusting the first target heater power downward by the adjustment value.

9. The method of claim 1, wherein the adjustment value is determined based on a magnitude of the average rate of change in pressure.

10. The method of claim 1, further comprising:
determining that the average rate of change in pressure has a magnitude greater than a threshold magnitude;
based on the determination, generating a notification indicating an issue with the cryogenic device.

11. The method of claim 10, wherein the average rate of change in pressure is negative, and wherein the notification identifies the issue as a depleted cryogen source based on the average rate of change in pressure.

12. The method of claim 10, wherein the average rate of change in pressure is positive, and wherein the notification identifies the issue as a blocked or impeded cryogen pathway based on the average rate of change in pressure.

13. The method of claim 1, wherein the first treatment cycle comprises a cooling phase and a recovery phase, and wherein the first target heater power is applied during the cooling phase.

14. A method for stabilizing pressure within a cryogenic device during a cryotherapy treatment, the method comprising:
receiving a first flow rate value, wherein the first flow rate value corresponds to an expected average mass flow rate of a cryogen through a first needle probe of the cryogenic device during a cryotherapy treatment cycle;
determining, based on the first flow rate value, a first target heater power to be applied to a heater associated with the cryogenic device for a first treatment cycle, wherein the heater is configured to heat the cryogen;
receiving an input for the first treatment cycle;
causing the cryogen to flow for a period of time toward the first needle probe in response to the input;
applying the first target heater power to the heater during the first treatment cycle so as to cause the heater to heat the cryogen and stabilize pressure within the cryogenic device during or after the first treatment cycle; and
determining a target duty cycle necessary for applying the first target heater power, wherein applying the first target heater power engages the heater for the target duty cycle;
wherein the target duty cycle is determined based on an output of an equation: Duty Cycle=$P_{Target} \times (R_{Heater}/V_{Heater}^2)$, wherein $P_{Target}$ is the first target heater power, $R_{Heater}$ is a resistance of the heater, and $V_{Heater}$ is a voltage across the heater, further comprising monitoring a voltage of a power source coupled to the heater so as to estimate a real-time value for $V_{Heater}$.

15. The method of claim 14, further comprising:
replacing the first needle probe with a second needle probe;
receiving a second flow rate value, wherein the second flow rate value corresponds to an expected average mass flow rate of a cryogen through the second needle probe during a cooling phase of a cryotherapy treatment cycle; and
determining, based on the second flow rate value, a new target heater power to be applied by the heater for a treatment cycle to be performed with the second needle probe.

16. A method for stabilizing pressure within a cryogenic device during a cryotherapy treatment, the method comprising:
receiving a first flow rate value, wherein the first flow rate value corresponds to an expected average mass flow rate of a cryogen through a first needle probe of the cryogenic device during a cryotherapy treatment cycle;
determining, based on the first flow rate value, a first target heater power to be applied to a heater associated with the cryogenic device for a first treatment cycle, wherein the heater is configured to heat the cryogen;
receiving an input for the first treatment cycle;
causing the cryogen to flow for a period of time toward the first needle probe in response to the input;
applying the first target heater power to the heater during the first treatment cycle so as to cause the heater to heat the cryogen and stabilize pressure within the cryogenic device during or after the first treatment cycle;
determining a first pressure of the cryogenic device prior to a cooling cycle of the first treatment cycle;
determining a second pressure of the cryogenic device prior to a cooling cycle of a second treatment cycle; and
calculating a second target heater power for the second treatment cycle, wherein the second target heater power is calculated at least in part by:
adjusting the first target heater power upward when the second pressure is lower than the first pressure; or
adjusting the first target heater power downward when the second pressure is greater than the first pressure.

17. A cryogenic device comprising:
a cryogen source including a pressurized cryogen;
a cryogen pathway configured to direct the cryogen toward a needle probe comprising one or more needles, wherein the cryogen is configured to deliver cryotherapy to a target tissue via the one or more needles;
a heater; and
a processor configured to:
receive a first flow rate value, wherein the first flow rate value corresponds to an expected average mass flow rate of a cryogen through a first needle probe of the cryogenic device during a cryotherapy treatment cycle;
determine, based on the first flow rate value, a first target heater power to be applied to a heater associated with the cryogenic device for a first treatment cycle, wherein the heater is configured to heat the cryogen;
receive an input for the first treatment cycle;
cause the cryogen to flow for a period of time toward the first needle probe in response to the input;
apply the first target heater power to the heater during the first treatment cycle so as to heat the cryogen and stabilize pressure within the cryogenic device during or after the first treatment cycle
receive pressure data from a pressure sensor of the cryogenic device during the first treatment cycle;
calculate, based on the received pressure data, an average rate of change in pressure during a cooling phase of the first treatment cycle; and
calculate a second target heater power for a second treatment cycle, wherein the second target heater power is calculated at least in part by adjusting the first target heater power upward or downward by an adjustment value based on the average rate of change in pressure.

18. The cryogenic device of claim 17, wherein the first target heater power is defined such that an average rate of change in pressure during a cooling cycle of the first treatment cycle remains within a predefined range.

19. The cryogenic device of claim 17, wherein the processor is further configured to determine that the average rate of change in pressure is negative, wherein the second target heater power is calculated at least in part by adjusting the first target heater power upward by the adjustment value.

20. The cryogenic device of claim 17, wherein the processor is further configured to determine that the average rate of change in pressure is positive, wherein the second target heater power is calculated at least in part by adjusting the first target heater power downward by the adjustment value.

* * * * *